United States Patent
Castaigne et al.

(10) Patent No.: US 10,980,892 B2
(45) Date of Patent: Apr. 20, 2021

(54) METHODS FOR THE TREATMENT OF LEPTOMENINGEAL CARCINOMATOSIS

(71) Applicant: Angiochem Inc., Westmount (CA)

(72) Inventors: Jean-Paul Castaigne, Mont-Royal (CA); Betty Lawrence, Bolton (CA); Priya Kumthekar, Chicago, IL (US)

(73) Assignee: Angiochem Inc., Westmount (CA)

( * ) Notice: Subject to any disclaimer, the term of this patent is extended or adjusted under 35 U.S.C. 154(b) by 0 days.

(21) Appl. No.: 15/737,188

(22) PCT Filed: Jun. 15, 2016

(86) PCT No.: PCT/US2016/037626
§ 371 (c)(1),
(2) Date: Dec. 15, 2017

(87) PCT Pub. No.: WO2016/205367
PCT Pub. Date: Dec. 22, 2016

(65) Prior Publication Data
US 2018/0161442 A1    Jun. 14, 2018

Related U.S. Application Data

(60) Provisional application No. 62/257,562, filed on Nov. 19, 2015, provisional application No. 62/175,948, filed on Jun. 15, 2015.

(51) Int. Cl.
| | |
|---|---|
| *A61K 47/64* | (2017.01) |
| *A61K 9/00* | (2006.01) |
| *A61K 45/06* | (2006.01) |
| *A61K 47/12* | (2006.01) |
| *A61K 47/26* | (2006.01) |
| *A61K 47/34* | (2017.01) |
| *A61P 35/00* | (2006.01) |
| *A61K 31/337* | (2006.01) |
| *A61N 5/10* | (2006.01) |

(52) U.S. Cl.
CPC .......... *A61K 47/64* (2017.08); *A61K 9/0019* (2013.01); *A61K 31/337* (2013.01); *A61K 45/06* (2013.01); *A61K 47/12* (2013.01); *A61K 47/26* (2013.01); *A61K 47/34* (2013.01); *A61N 5/10* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 3,953,417 A | 4/1976 | Konig et al. | |
| 4,671,958 A | 6/1987 | Rodwell et al. | |
| 4,801,575 A | 1/1989 | Pardridge | |
| 4,902,505 A | 2/1990 | Pardridge et al. | |
| 4,935,465 A | 6/1990 | Garman | |
| 4,942,184 A | 7/1990 | Haugwitz et al. | |
| 5,028,697 A | 7/1991 | Johnson et al. | |
| 5,041,424 A | 8/1991 | Saulnier et al. | |
| 5,118,668 A | 6/1992 | Auerswald et al. | |
| 5,126,249 A | 6/1992 | Becker et al. | |
| 5,169,933 A | 12/1992 | Anderson et al. | |
| 5,204,354 A | 4/1993 | Chakravarty et al. | |
| 5,223,409 A | 6/1993 | Ladner et al. | |
| 5,258,499 A | 11/1993 | Konigsberg et al. | |
| 5,362,831 A | 11/1994 | Mongelli et al. | |
| 5,442,043 A | 8/1995 | Fukuta et al. | |
| 5,506,120 A | 4/1996 | Yamamoto et al. | |
| 5,578,451 A | 11/1996 | Nishimoto | |
| 5,620,884 A | 4/1997 | Shorr et al. | |
| 5,627,270 A | 5/1997 | Kahne et al. | |
| RE35,524 E | 6/1997 | Saulnier et al. | |
| 5,683,694 A | 11/1997 | Bagshawe et al. | |
| 5,780,265 A | 7/1998 | Dennis et al. | |
| 5,807,980 A | 9/1998 | Lasters et al. | |
| 5,869,045 A | 2/1999 | Hellstrom et al. | |
| 5,908,832 A | 6/1999 | Payza et al. | |
| 5,922,754 A | 7/1999 | Burchett et al. | |
| 5,948,750 A | 9/1999 | Garsky et al. | |
| 5,948,888 A | 9/1999 | de la Monte et al. | |
| 5,955,444 A | 9/1999 | Ingram et al. | |
| 5,962,266 A | 10/1999 | White et al. | |
| 5,981,564 A | 11/1999 | Page et al. | |
| 6,093,692 A | 7/2000 | Shen et al. | |
| 6,126,965 A | 10/2000 | Kasid et al. | |
| 6,191,290 B1 | 2/2001 | Safavy | |
| 6,245,359 B1 | 6/2001 | Milstein et al. | |
| 6,290,961 B1 | 9/2001 | Aoki et al. | |
| 6,306,993 B1 | 10/2001 | Rothbard et al. | |
| 6,310,039 B1 | 10/2001 | Kratz | |

(Continued)

FOREIGN PATENT DOCUMENTS

| | | |
|---|---|---|
| CN | 102406949 A | 4/2012 |
| CN | 102552928 A | 7/2012 |

(Continued)

OTHER PUBLICATIONS

Hudis "Triple-Negative Breast Cancer: An Unmet Medical Need" oncologist 16(suppl 1): 1-11 (Year: 2011).*

Walbert "The role of chemotherapy in the treatment of patients with brain metastases from solid tumors" intj clin oncol 14:299-306 (Year: 2009).*

Regina "Antitumour activity of ANG1005, a conjugate between paclitaxel and the new brain delivery vector Angiopep-2" britj pharma 155:185-197 (Year: 2008).*

Mehta "Therapeutic approaches for HER2-positive brain metastases: Circumventing the blood-brain barrier" cancer treat rev 39(3): 261-269 (Year: 2013).*

(Continued)

*Primary Examiner* — Adam Weidner
(74) *Attorney, Agent, or Firm* — Clark & Elbing LLP

(57) ABSTRACT

The present invention features a method of treating leptomeningeal carcinomatosis in a subject using a peptide-therapeutic conjugate as exemplified by the agent ANG1005.

19 Claims, 4 Drawing Sheets
Specification includes a Sequence Listing.

(56) References Cited

U.S. PATENT DOCUMENTS

| | | |
|---|---|---|
| 6,316,024 B1 | 11/2001 | Allen et al. |
| 6,348,207 B1 | 2/2002 | Milstein et al. |
| 6,372,250 B1 | 4/2002 | Pardridge |
| 6,376,648 B2 | 4/2002 | White et al. |
| 6,391,305 B1 | 5/2002 | Feng et al. |
| 6,391,913 B1 | 5/2002 | Page et al. |
| 6,469,047 B1 | 10/2002 | Jackson et al. |
| 6,475,481 B2 | 11/2002 | Talmadge |
| 6,475,781 B1 | 11/2002 | Mercola et al. |
| 6,495,513 B1 | 12/2002 | Rueger et al. |
| 6,613,890 B2 | 9/2003 | White et al. |
| 6,660,525 B2 | 12/2003 | Martin et al. |
| 6,689,582 B1 | 2/2004 | Davies et al. |
| 6,713,454 B1 | 3/2004 | Ekwuribe et al. |
| 6,906,033 B2 | 6/2005 | White et al. |
| 6,929,919 B2 | 8/2005 | St George-Hyslop et al. |
| 6,930,090 B2 | 8/2005 | Ekwuribe et al. |
| 7,019,123 B2 | 3/2006 | Tamburini et al. |
| 7,049,058 B2 | 5/2006 | Singh |
| 7,067,632 B2 | 6/2006 | Elliott |
| 7,101,844 B2 | 9/2006 | Kim et al. |
| 7,115,707 B2 | 10/2006 | Ben-Sasson et al. |
| 7,153,946 B2 | 12/2006 | McChesney et al. |
| 7,192,921 B2 | 3/2007 | Laakkonen et al. |
| 7,208,174 B2 | 4/2007 | Huwyler et al. |
| 7,214,657 B2 | 5/2007 | Kream |
| 7,271,149 B2 | 9/2007 | Glaesner et al. |
| 7,319,090 B2 | 1/2008 | Katz |
| 7,557,182 B2 | 7/2009 | Beliveau et al. |
| 7,569,544 B2 | 8/2009 | Zankel et al. |
| 7,700,554 B2 | 4/2010 | Beliveau et al. |
| 7,902,156 B2 | 3/2011 | Beliveau et al. |
| 8,530,429 B2 | 9/2013 | Robbins et al. |
| 8,569,323 B2 | 10/2013 | Ren et al. |
| 8,828,925 B2 | 9/2014 | Demeule et al. |
| 8,834,874 B2 | 9/2014 | Pardridge et al. |
| 9,173,891 B2 | 11/2015 | Castaigne et al. |
| 2002/0013260 A1 | 1/2002 | Jia |
| 2002/0041898 A1 | 4/2002 | Unger et al. |
| 2002/0086384 A1 | 7/2002 | Levine et al. |
| 2002/0156124 A1 | 10/2002 | Gao et al. |
| 2003/0129186 A1 | 7/2003 | Beliveau et al. |
| 2003/0170891 A1 | 9/2003 | McSwiggen |
| 2003/0220391 A1 | 11/2003 | Bogardus et al. |
| 2004/0052814 A1 | 3/2004 | Shi et al. |
| 2004/0058865 A1 | 3/2004 | Danishefsky et al. |
| 2004/0077540 A1 | 4/2004 | Quay |
| 2004/0087499 A1 | 5/2004 | Laakkonen et al. |
| 2004/0101904 A1 | 5/2004 | Pardridge et al. |
| 2004/0102369 A1 | 5/2004 | Wu et al. |
| 2004/0146549 A1 | 7/2004 | Ben-Sasson et al. |
| 2004/0162284 A1 | 8/2004 | Harris et al. |
| 2004/0220132 A1 | 11/2004 | Kaemmerer |
| 2004/0241174 A1 | 12/2004 | Amphlett et al. |
| 2005/0026823 A1 | 2/2005 | Zankel et al. |
| 2005/0042227 A1 | 2/2005 | Zankel et al. |
| 2005/0058702 A1 | 3/2005 | Ben-Sasson et al. |
| 2005/0100986 A1 | 5/2005 | Verma et al. |
| 2005/0107325 A1 | 5/2005 | Manoharan et al. |
| 2005/0178395 A1 | 8/2005 | Hunter et al. |
| 2005/0183731 A1 | 8/2005 | Hunter et al. |
| 2005/0215478 A1 | 9/2005 | Ben-Sasson et al. |
| 2006/0019347 A1 | 1/2006 | Cho et al. |
| 2006/0029609 A1 | 2/2006 | Zankel et al. |
| 2006/0135428 A1 | 6/2006 | Bridon et al. |
| 2006/0182684 A1 | 8/2006 | Beliveau |
| 2006/0189515 A1 | 8/2006 | Beliveau et al. |
| 2006/0251713 A1 | 11/2006 | Ben-Sasson et al. |
| 2007/0031844 A1 | 2/2007 | Khvorova et al. |
| 2007/0149444 A1 | 6/2007 | Laakkonen et al. |
| 2007/0167365 A1 | 7/2007 | Beliveau et al. |
| 2007/0172462 A1 | 7/2007 | Bohn et al. |
| 2007/0197460 A1 | 8/2007 | Fougerolles et al. |
| 2007/0207958 A1 | 9/2007 | Bridon et al. |
| 2008/0014143 A1 | 1/2008 | Ruoslahti et al. |
| 2008/0199436 A1 | 8/2008 | Sawada |
| 2008/0213185 A1 | 9/2008 | Hong et al. |
| 2008/0299039 A1 | 12/2008 | Beliveau et al. |
| 2009/0016959 A1 | 1/2009 | Beliveau et al. |
| 2009/0021883 A1 | 1/2009 | Delida |
| 2009/0082277 A1 | 3/2009 | Beliveau et al. |
| 2009/0215883 A1 | 8/2009 | Bouzada et al. |
| 2009/0221477 A1 | 9/2009 | Artymiuk et al. |
| 2009/0246211 A1 | 10/2009 | Henri et al. |
| 2010/0209429 A1 | 8/2010 | Erlich et al. |
| 2010/0256055 A1 | 10/2010 | Castaigne et al. |
| 2010/0284921 A1 | 11/2010 | Gordon et al. |
| 2010/0297120 A1 | 11/2010 | Beliveau et al. |
| 2011/0039785 A1 | 2/2011 | Beliveau et al. |
| 2011/0059187 A1 | 3/2011 | Basu et al. |
| 2011/0112036 A1 | 5/2011 | Demeule et al. |
| 2011/0171128 A1 | 7/2011 | Beliveau et al. |
| 2011/0218152 A1 | 9/2011 | Beliveau et al. |
| 2011/0305750 A1 | 12/2011 | Beliveau et al. |
| 2011/0318322 A1 | 12/2011 | Bossard |
| 2012/0015876 A1 | 1/2012 | Castaigne et al. |
| 2012/0122798 A1 | 5/2012 | Castaigne et al. |
| 2012/0156130 A1 | 6/2012 | Hettmann et al. |
| 2012/0245169 A1 | 9/2012 | Ren et al. |
| 2013/0022546 A1 | 1/2013 | Wall et al. |
| 2013/0029982 A1 | 1/2013 | Castro et al. |
| 2013/0029984 A1 | 1/2013 | Castro et al. |
| 2013/0034548 A1 | 2/2013 | Moyo et al. |
| 2013/0034572 A1 | 2/2013 | Stanimirovic et al. |
| 2013/0035069 A1 | 2/2013 | Fisher |
| 2013/0045873 A1 | 2/2013 | Hood et al. |
| 2013/0122056 A1 | 5/2013 | Zhang et al. |
| 2013/0150314 A1 | 6/2013 | Myers et al. |
| 2013/0177499 A1 | 7/2013 | Brahmbhatt et al. |
| 2013/0195761 A1 | 8/2013 | Pereira et al. |
| 2014/0017166 A1 | 1/2014 | Hettmann et al. |
| 2014/0086921 A1 | 3/2014 | Griswold-Prenner et al. |
| 2014/0099303 A1 | 4/2014 | Griswold-Prenner et al. |
| 2014/0099304 A1 | 4/2014 | Griswold-Prenner et al. |
| 2014/0100214 A1 | 4/2014 | Castro et al. |
| 2014/0120083 A1 | 5/2014 | Stern et al. |
| 2014/0127196 A1 | 5/2014 | Van Vlasselaer et al. |
| 2014/0127208 A1 | 5/2014 | Van Vlasselaer et al. |
| 2014/0140933 A1 | 5/2014 | Van Vlasselaer et al. |
| 2014/0355163 A1 | 12/2014 | Chung |
| 2015/0037311 A1 | 2/2015 | Boivin et al. |
| 2015/0038429 A1 | 2/2015 | Demeule et al. |

FOREIGN PATENT DOCUMENTS

| | | |
|---|---|---|
| CN | 102614105 A | 8/2012 |
| DE | 2344886 A1 | 4/1975 |
| DE | 19953696 A1 | 5/2001 |
| EP | 0393431 A1 | 10/1990 |
| EP | 1466924 A1 | 10/2004 |
| GB | 2360453 A | 9/2001 |
| JP | H10-236984 A | 9/1998 |
| WO | WO-87/05702 A1 | 9/1987 |
| WO | WO-92/02539 A1 | 2/1992 |
| WO | WO-92/16555 A1 | 10/1992 |
| WO | WO-96/31531 A2 | 10/1996 |
| WO | WO-96/35788 A2 | 11/1996 |
| WO | WO-96/39160 A1 | 12/1996 |
| WO | WO-96/39183 A1 | 12/1996 |
| WO | WO-96/40210 A1 | 12/1996 |
| WO | WO-97/33996 A2 | 9/1997 |
| WO | WO-97/40160 A1 | 10/1997 |
| WO | WO-97/40854 A2 | 11/1997 |
| WO | WO-98/39469 A1 | 9/1998 |
| WO | WO-99/46575 A2 | 9/1999 |
| WO | WO-00/01417 A1 | 1/2000 |
| WO | WO-00/71574 A2 | 11/2000 |
| WO | WO-01/30319 A1 | 5/2001 |
| WO | WO-02/13873 A2 | 2/2002 |
| WO | WO-02/33090 A2 | 4/2002 |
| WO | WO-02/38144 A2 | 5/2002 |
| WO | WO-00/24782 A3 | 6/2002 |
| WO | WO-02/43765 A2 | 6/2002 |
| WO | WO-02/085923 A2 | 10/2002 |

(56) References Cited

FOREIGN PATENT DOCUMENTS

| | | |
|---|---|---|
| WO | WO-03/009815 A2 | 2/2003 |
| WO | WO-03/032913 A2 | 4/2003 |
| WO | WO-03/066859 A2 | 8/2003 |
| WO | WO-03/102583 A1 | 12/2003 |
| WO | WO-2004/060403 A2 | 7/2004 |
| WO | WO-2004/091623 A1 | 10/2004 |
| WO | WO-2004/093897 A1 | 11/2004 |
| WO | WO-2004/108071 A2 | 12/2004 |
| WO | WO-2005/000360 A2 | 1/2005 |
| WO | WO-2005/002515 A2 | 1/2005 |
| WO | WO-2005/014625 A1 | 2/2005 |
| WO | WO-2005/021579 A2 | 3/2005 |
| WO | WO-2005/042029 A2 | 5/2005 |
| WO | WO-2006/009902 A2 | 1/2006 |
| WO | WO-2006/086870 A1 | 8/2006 |
| WO | WO-2006/089290 A1 | 8/2006 |
| WO | WO-2006/108052 A2 | 10/2006 |
| WO | WO-2006/138343 A2 | 12/2006 |
| WO | WO-2007/009229 A1 | 1/2007 |
| WO | WO-2007/020085 A2 | 2/2007 |
| WO | WO-2007/030619 A2 | 3/2007 |
| WO | WO-2007/035716 A2 | 3/2007 |
| WO | WO-2007/044323 A2 | 4/2007 |
| WO | WO-2007/070672 A2 | 6/2007 |
| WO | WO-2007/082978 A1 | 7/2007 |
| WO | WO-2007/082979 A1 | 7/2007 |
| WO | WO-2007/103515 A2 | 9/2007 |
| WO | WO-2007/113172 A2 | 10/2007 |
| WO | WO-2007/140282 A1 | 12/2007 |
| WO | WO-2008/011633 A2 | 1/2008 |
| WO | WO-2008/012629 A1 | 1/2008 |
| WO | WO-2008/036682 A2 | 3/2008 |
| WO | WO-2008/046228 A1 | 4/2008 |
| WO | WO-2008/069876 A2 | 6/2008 |
| WO | WO-2008/116171 A1 | 9/2008 |
| WO | WO-2008/144919 A1 | 12/2008 |
| WO | WO-2009/039188 A1 | 3/2009 |
| WO | WO-2009/046220 A2 | 4/2009 |
| WO | WO-2009/070597 A2 | 6/2009 |
| WO | WO-2009/079790 A1 | 7/2009 |
| WO | WO-2009/105671 A2 | 8/2009 |
| WO | WO-2009/127072 A1 | 10/2009 |
| WO | WO-2010/006239 A2 | 1/2010 |
| WO | WO-2010/043047 A1 | 4/2010 |
| WO | WO-2010/043049 A1 | 4/2010 |
| WO | WO-2010/063122 A1 | 6/2010 |
| WO | WO-2010/063123 A1 | 6/2010 |
| WO | WO-2010/063124 A1 | 6/2010 |
| WO | WO-2010/069074 A1 | 6/2010 |
| WO | WO-2010/080720 A2 | 7/2010 |
| WO | WO-2010/121379 A1 | 10/2010 |
| WO | WO-2010/142035 A1 | 12/2010 |
| WO | WO-2011/000095 A1 | 1/2011 |
| WO | WO-2011/008823 A2 | 1/2011 |
| WO | WO-2011/041897 A1 | 4/2011 |
| WO | WO-2011/060206 A2 | 5/2011 |
| WO | WO-2011/063507 A1 | 6/2011 |
| WO | WO-2011/073199 A1 | 6/2011 |
| WO | WO-2011/112615 A1 | 9/2011 |
| WO | WO-2011/153642 A1 | 12/2011 |
| WO | WO-2012/000118 A1 | 1/2012 |
| WO | WO-2012/006239 A1 | 1/2012 |
| WO | WO-2012/037687 A1 | 3/2012 |
| WO | WO-2012/064973 A2 | 5/2012 |
| WO | WO-2012/068531 A2 | 5/2012 |
| WO | WO-2012/097000 A1 | 7/2012 |
| WO | WO-2012/118376 A1 | 9/2012 |
| WO | WO-2012/135025 A2 | 10/2012 |
| WO | WO-2012/138694 A2 | 10/2012 |
| WO | WO-2012/149267 A1 | 11/2012 |
| WO | WO-2012/153286 A1 | 11/2012 |
| WO | WO-2012/162807 A1 | 12/2012 |
| WO | WO-2013/004716 A1 | 1/2013 |
| WO | WO-2013/012915 A1 | 1/2013 |
| WO | WO-2013/012918 A1 | 1/2013 |
| WO | WO-2013/023184 A1 | 2/2013 |
| WO | WO-2013/032591 A1 | 3/2013 |
| WO | WO-2013/043232 A2 | 3/2013 |
| WO | WO-2013/049332 A1 | 4/2013 |
| WO | WO-2013/056096 A1 | 4/2013 |
| WO | WO-2013/063468 A1 | 5/2013 |
| WO | WO-2013/071272 A1 | 5/2013 |
| WO | WO-2013/078562 A2 | 6/2013 |
| WO | WO-2013/078564 A2 | 6/2013 |
| WO | WO-2013/090861 A1 | 6/2013 |
| WO | WO-2013/120107 A1 | 8/2013 |
| WO | WO-2013/131032 A1 | 9/2013 |
| WO | WO-2013/151774 A1 | 10/2013 |
| WO | WO-2013/162757 A1 | 10/2013 |
| WO | WO-2013/185235 A1 | 12/2013 |
| WO | WO-2014/026283 A1 | 2/2014 |
| WO | WO-2014/026286 A1 | 2/2014 |
| WO | WO-2014/028487 A1 | 2/2014 |
| WO | WO-2014/028777 A2 | 2/2014 |
| WO | WO-2014/071109 A1 | 5/2014 |
| WO | WO-2014/071206 A1 | 5/2014 |
| WO | WO-2014/071531 A1 | 5/2014 |
| WO | WO-2014/076655 A1 | 5/2014 |
| WO | WO-2014/082065 A1 | 5/2014 |
| WO | WO-2014/082163 A1 | 6/2014 |
| WO | WO-2014/082184 A1 | 6/2014 |
| WO | WO-2014/194428 A1 | 12/2014 |
| WO | WO-2014/194429 A1 | 12/2014 |

OTHER PUBLICATIONS

Kurzrock "Safety, Pharmacokinetics, and Activity of GRN1005, a Novel Conjugate of Angiopep-2, a Peptide Facilitating Brain Penetration, and Paclitaxel, in Patients with Advanced Solid Tumors" mol cancer ther 11 (2):308-316 (Year: 2012).*

U.S. Appl. No. 61/138,375, Beliveau et al.

U.S. Appl. No. 61/546,851, filed Oct. 13, 2011, Demuele et al.

"Breast Cancer: 7 Myths Debunked," <http://kaldascenter.com/media/Kaldas-Center-Breast-Cancer.pdf>, retrieved Jun. 30, 2015 (1 page).

"Childhood Cancer (ChiCa)," UICC, <http://www.uicc.org/programmes/childhood-cancer>, retrieved Jun. 30, 2015 (1 page).

"What Are the Signs of Cancer in Pets," Home Vet, <http://www.homevet.com/pet-care-library/item/382-what-are-the-signs-of-cancer-in-pets>, retrieved Jun. 30, 2015 (3 pages).

"Why two thirds of cancer cases are not preventable," Chewy Chunks, <https://chewychunks.wordpress.com/2015/01/30/why-two-thirds-of-cancer-cases-are-not-preventable/>, retrieved Jun. 30, 2015 (4 pages).

Akhtar et al., "Nonviral delivery of synthetic siRNAs in vivo," J Clin Invest. 117(12):3623-32 (2007).

Amenta et al., "Tests to localize free proteolytic enzymes in vivo by 14C-cysteine-aprotinin," Adv Exp Med Biol. 120B:379-83 (1979) (Abstract only).

American College of Rheumatology Subcommittee on Rheumatoid Arthritis Guidelines, "Guidelines for the management of rheumatoid arthritis: 2002 update," Arthritis & Rheum. 46(2):328-46 (2002).

Anonymous, "Blood-Brain Barrier Tackled," <http://www.ecancermedicalscience.com/news-insider-news.asp?itemId=326>, published Oct. 22, 2008 (2 pages).

Arpicco et al., "New coupling reagents for the preparation of disulfide cross-linked conjugates with increased stability," Bioconjug Chem. 8(3):327-37 (1997).

Arseneault et al., "Synthesis of a controlled three-faced PAMAM particle," Polym Chem. 2:2293-8 (2011).

Back et al., "The effect of aprotinin on the harmine-induced tremor in lymphostatic encephalopathic and normal rats," Eur J Pharmacol. 32(02):365-9 (1975).

Ballabh et al., "The blood-brain barrier: an overview: structure, regulation, and clinical implications," Neurobiol Dis. 16(1):1-13 (2004).

Banks, "Leptin transport across the blood-brain barrier: implications for the cause and treatment of obesity," Curr Pharm Des. 7(2):125-33 (2001).

(56) References Cited

OTHER PUBLICATIONS

Banks, "The blood-brain barrier as a cause of obesity," Curr Pharm Des. 14(16):1606-14 (2008).
Barakat et al., "Modulation of p-glycoprotein function by caveolin-1 phosphorylation," J Neurochem. 101(1):1-8 (2007).
Becker, "Putative antigenic domains in glycoprotein G of rabies virus: is the RGK sequence involved in virus adsorption to cellular receptors?," Virus Genes. 3(3):277-84 (1990).
Bertrand et al., "Transport characteristics of a novel peptide platform for CNS therapeutics," J Cell Mol Med. 14(12):2827-39 (2010).
Bicamumpaka et al., "In vitro cytotoxicity of paclitaxel-transferrin conjugate on H69 cells," Oncol Rep. 5(6):1381-3 (1998).
Bickel et al., "Delivery of peptides and proteins through the blood-brain barrier," Adv Drug Deliv Rev. 46(1-3):247-279 (2001).
Boado et al., "GDNF fusion protein for targeted-drug delivery across the human blood-brain barrier," Biotechnol Bioeng. 100(2):387-96 (2008).
Boado, "Blood-brain barrier transport of non-viral gene and RNAi therapeutics," Pharm Res. 24(9):1772-87 (2007).
Bork et al., "Go hunting in sequence databases but watch out for the traps," Trends Genet. 12:425-427 (1996).
Bork, "Powers and pitfalls in sequence analysis: the 70% hurdle," Genome Research 10, 398-400, 2000.
Brady et al., "Drug design. Reflections on a peptide," Nature. 368(6473):692-693 (1994).
Brenner, "Errors in Genome Annotation," Trends Genet. 15(4):132-3 (1999).
Castaigne et al., "425 Poster ANG1005: Preliminary clinical safety and tolerability in patients with recurrent malignant glioma," Eur J Cancer. 6(12):133-134 (2008).
Castex et al., "2-Pyrrolinodoxorubicin and its peptide-vectorized form bypass multidrug resistance," Anticancer Drugs. 15(6):609-617 (2004).
Chari, "Targeted Cancer Therapy: Conferring Specificity to Cytotoxic Drugs," Acc. Chem. Res. 41:98-107 (2008).
Chen et al., "Synthesis of doxorubicin conjugates through hydrazone bonds to melanotransferrin P97," Synth Commun. 33(14):2377-2390 (2003).
Cho et al., "An unnatural biopolymer," Science. 261(5126):1303-1305 (1993).
Chu et al., "$^1$H NMR spectra of diastereomeric aromatic dipeptides (Phe-Phe) in aqueous solution," Magn Reson Chem. 23(6):450-3 (1985).
Chu et al., "Detection of soluble P-glycoprotein in culture media and extracellular fluids," Biochem Biophys Res Commun. 203(1):506-512 (1994).
Ché et al., "New Angiopep-modified doxorubicin (ANG1007) and etoposide (ANG1009) chemotherapeutics with increased brain penetration" J Med Chem. 53(7):2814-24 (2010).
Comereski et al., "BR96-doxorubicin conjugate (BMS-182248) versus doxorubicin: a comparative toxicity assessment in rats," Toxicol Pathol. 22(5):473-88 (1994).
Coon et al., "Solutol HS 15, nontoxic polyoxyethylene esters of 12-hydroxystearic acid, reverses multidrug resistance," Cancer Res. 51(3):897-902 (1991).
Cui et al., "PAMAM-drug complex for delivering anticancer drug across blood-brain barrier in-vitro and in-vivo," Afr J Pharm Pharmacol. 3(5):227-233 (2009).
Cull et al., "Screening for receptor ligands using large libraries of peptides linked to the C terminus of the lac repressor," Proc Natl Acad Sci U S A. 89(5): 1865-1869 (1992).
D'Onofrio et al., "Glycomimetics as decorating motifs for oligonucleotides: solid-phase synthesis, stability, and hybridization properties of carbopeptoid-oligonucleotide conjugates," Bioconjug Chem. 16(5):1299-1309 (2005).
Dagenais et al., "Development of an in situ mouse brain perfusion model and its application to mdr1a P-glycoprotein-deficient mice," J Cereb Blood Flow Metab. 20(2):381-386 (2000).

Deane et al., "LRP/Amyloid beta-Peptide interaction mediates differential brain efflux of A(beta) isoforms," Neuron. 43:333-344 (2004).
Dehouck et al., "A new function for the LDL receptor: transcytosis of LDL across the blood-brain barrier," J Cell Biol. 138(4):877-889 (1997).
Dehouck et al., "An easier, reproducible, and mass-production method to study the blood-brain barrier in vitro," J Neurochem. 54(5):1798-1801 (1990).
Dehouck et al., "Drug transfer across the blood-brain barrier: correlation between in vitro and in vivo models," J Neurochem. 58(5):1790-1797 (1992).
Demeule et al., "ANG2002: A new Angiochem-modified neurotensin with increased brain penetration and analgesic properties," Program No. 374.11/QQ6 2010 Neuroscience Meeting Planner, San Diego, CA: Society for Neuroscience (2010) (5 pages).
Demeule et al., "Conjugation of a brain-penetrant peptide with neurotensin provides antinociceptive properties," J Clin Invest. 124(3):1199-1213 (2014) (15 pages).
Demeule et al., "Drug transport to the brain: key roles for the efflux pump P-glycoprotein in the blood-brain barrier," Vascul Pharmacol. 38(6):339-48 (2002).
Demeule et al., "High transcytosis of melanotransferrin (P97) across the blood-brain barrier," J Neurochem. 83(4):924-933 (2002).
Demeule et al., "Identification and design of peptides as a new drug delivery system for the brain," J Pharmacol Exp Ther. 324(3):1064-1072 (2008).
Demeule et al., "Involvement of the low-density lipoprotein receptor-related protein in the transcytosis of the brain delivery vector angiopep-2," J Neurochem. 106(4):1534-44 (2008).
Demeule et al., "Isolation of endothelial cells from brain, lung, and kidney: expression of the multidrug resistance P-Glycoprotein isoforms," Biochem Biophys Res Commun. 281(3):827-834 (2001).
Deng et al., "Selected cysteine residues in transmembrane domains of mu-opioid receptor are critical for effects of sulfhydryl reagents," J Pharm Exp Ther. 293(1):113-20 (2000).
Derossi et al., "The third helix of the Antennapedia homeodomain translocates through biological membranes," J Biol Chem. 269(14):10444-50 (1994).
DeWitt et al., "'Diversomers': an approach to nonpeptide, nonoligomeric chemical diversity," Proc Natl Acad Sci U S A. 90(15):6909-6913 (1993).
Doerks et al., "Protein annotation: detective work for function prediction," Trends Genet. 14:248-250 (1998).
Dooley et al., "An all D-amino acid opioid peptide with central analgesic activity from a combinatorial library," Science. 266(5193):2019-22 (1994).
Egami, "The effect of proteolytic enzyme inhibitor on experimental brain swelling," Bull Yamaguchi Med School. 17(3-4):207-38 (1970).
Egger-Heigold, Barbara, Thesis: "The effect of excipients on pharmacokinetic parameters of parenteral drugs," Doctorate, University of Basel, 2005 (89 Pages).
Egleton et al., "Development of neuropeptide drugs that cross the blood-brain barrier," NeuroRx 2(1):44-53 (2005).
Fellner et al., "Transport of paclitaxel (Taxol) across the blood-brain barrier in vitro and in vivo," J Clin Invest. 110(9):1309-18 (2002).
Fillebeen et al., "Receptor-mediated transcytosis of lactoferrin through the blood-brain barrier," J Biol Chem. 274(11):7011-7017 (1999).
Fioretti et al., "Aprotinin-like isoinhibitors in bovine organs," Biol Chem Hoppe Seyler. 369 Suppl:37-42 (1988).
Fromm, "P-glycoprotein: a defense mechanism limiting oral bioavailability and CNS accumulation of drugs," Int J Clin Pharmacol Ther. 38(2):69-74 (2000).
Gabathuler et al., "117 Poster ANG1005, Paclitaxel conjugated to the angiopep brain transport vector for the treatment of brain cancer: preclinical studies," Eur J Cancer. 6(12):38-9 (2008).
Gabathuler et al., "147 Poster a new Taxol delivery system for the treatment of brain primary or metastatic tumors," Eur J Cancer. 4(12):47-8 (2006).
Gabathuler et al., "A new drug, ANG1005, a conjugate of Paclitaxel and Angiopep peptide vector able to cross the Blood-Brain Barrier for the treatment of brain cancers," <http://angiochem.com/sites/

(56) References Cited

OTHER PUBLICATIONS default/files/publications/BBB_Oregon_18-21%20Mar_09.pdf>, retrieved Sep. 16, 2016, Neuro-Onco. 10: 784 (2008) (1 page).
Gabathuler, "Approaches to transport therapeutic drugs across the blood-brain barrier to treat brain diseases," Neurobiol Dis. 37(1):48-57 (2010).
Gabius et al., "Targeting of neoglycoprotein-drug conjugates to cultured human embryonal carcinoma cells," J Cancer Res Clin Oncol. 113(2):126-130 (1987).
Gaillard et al., "Targeted delivery across the blood-brain barrier," Expert Opin Drug Deliv. 2(2):299-309 (2005).
Gallop et al., "Applications of combinatorial technologies to drug discovery. 1. Background and peptide combinatorial libraries," J Med Chem. 37(9):1233-1251 (1994).
Gavrilov et al., "Therapeutic siRNA: principles, challenges, and strategies," Yale J Biol Med. 85(2):187-200 (2012).
Gelmon, "The taxoids: paclitaxel and docetaxel," Lancet. 344:1267-1272 (1994).
Gottschalk et al., "Protein self-association in solution: the bovine pancreatic trypsin inhibitor decamer," Biophys J. 84(6):3941-58 (2003).
Grabb et al., "Neoplastic and pharmacological influence on the permeability of an in vitro blood-brain barrier," J Neurosurg. 82(6):1053-1058 (1995).
Grimm et al., "Ten year biochemical outcomes following 125-iodine monotherapy for early stage prostate cancer," Proceedings of the 42nd Annual ASTRO Meeting, Int J Rad Oncol Biol Phys. 48(3):145-7 Supplement (2000) (2 Pages).
Guillot et al., "Angiotensin peptide regulation of bovine brain microvessel endothelial cell monolayer permeability," J Cardiovasc Pharmacol. 18(2):212-218 (1991).
Gumbleton et al., "Progress and limitations in the use of in vitro cell cultures to serve as a permeability screen for the blood-brain barrier," J Pharm Sci. 90(11):1681-1698 (2001).
Halab et al., "Design, synthesis, and conformational analysis of azacycloalkane amino acids as conformationally constrained probes for mimicry of peptide secondary structures," Biopolymers. 55(2):101-122 (2000).
Haspel et al., "System for cleavable Fc fusion proteins using tobacco etch virus (TEV) protease," Biotechniques. 30(1):60, 61, 64-66 (2001).
Hawkins et al., "The blood-brain barrier/neurovascular unit in health and disease," Pharmacol Rev. 57(2):173-185 (2005).
Henderson et al., "Terminal amino acid sequences and proteolytic cleavage sites of mouse mammary tumor virus env gene products," J Virol. 48(1):314-9 (1983).
Huang et al., "Dual targeting effect of Angiopep-2-modified, DNA-loaded nanoparticles for glioma," Biomaterials. 32:6832-8 (2011).
Huang et al., "Targeting delivery of paclitaxel into tumor cells via somatostatin receptor endocytosis," Chem Biol. 7(7):453-61 (2000).
Hussain et al., "The mammalian low-density lipoprotein receptor family," Annu Rev Nutr. 19:141-172 (1999).
International Search Report and Written Opinion for International Application No. PCT/US16/37626, dated Oct. 7, 2016 (13 pages).
Ito et al., "Functional characterization of the brain-to-blood efflux clearance of human amyloid-beta peptide (1-40) across the rat blood-brain barrier," Neurosci Res. 56:246-252 (2006).
Jameson et al., "A rationally designed CD4 analogue inhibits experimental allergic encephalomyelitis," Nature. 368(6473):744-746 (1994).
Jiang et al., "Tumor cell targeting of transferrin-PEG-TNF-alpha conjugate via a receptor-mediated delivery system: design, synthesis, and biological evaluation," Bioconjug Chem. 18(1):41-9 (2007).
Jodoin et al., "P-glycoprotein in blood-brain barrier endothelial cells: interaction and oligomerization with caveolins," J Neurochem. 87(4):1010-23 (2003).
Kalra, "Central leptin insufficiency syndrome: an interactive etiology for obesity, metabolic and neural diseases and for designing new therapeutic interventions," Peptides. 29(1):127-38 (2008).

Kamps et al., "Uptake of long-circulating immunoliposomes, directed against colon adenocarcinoma cells, by liver metastases of colon cancer," J Drug Target. 8(4):235-245 (2000).
Karyekar et al., "Zonula occludens toxin increases the permeability of molecular weight markers and chemotherapeutic agents across the bovine brain microvessel endothelial cells," J Pharm Sci. 92(2):414-23 (2003).
Ke et al., "Gene delivery targeted to the brain using an angiopep-conjugated polyethyleneglycol-modified polyamidoamine dendrimer," Biomaterials. 30(36):6976-85 (2009).
Kiernan et al., "Fluorescent-labelled aprotinin: A new reagent for the histochemical detection of acid mucosubstances," Histochemie. 34(1): 77-84 (1973).
Kirpotin et al., "Sterically stabilized anti-HER2 immunoliposomes: design and targeting to human breast cancer cells in vitro," Biochemistry. 36(1):66-75 (1997).
Kirsch et al., "Anti-angiogenic treatment strategies for malignant brain tumors," J Neurooncol. 50(1-2):149-63 (2000).
Knapton, "Let's stop trying to cure cancer, says cancer professor," The Telegraph, <http://www.telegraph.co.uk/science/2016/03/15/lets-stop-trying-to-cure-cancer-says-cancer-professor/>, retrieved Jun. 7, 2018 (3 pages).
Kounnas et al., "LDL receptor-related protein, a multifunctional ApoE receptor, binds secreted beta-amyloid precursor protein and mediates Its degradation," Cell. 82(2):331-340 (1995).
Koziara et al., "In situ blood-brain barrier transport of nanoparticles," Pharm Res. 20(11):1772-1778 (2003).
Kreuter et al., "Apolipoprotein-mediated transport of nanoparticle-bound drugs across the blood-brain barrier," J Drug Target. 10(4):317-325 (2002).
Kreuter et al., "Direct evidence that polysorbate-80-coated poly(Butylcyanoacrylate) nanoparticles deliver drugs to the CNS via specific mechanisms requiring prior binding of drug to the nanoparticles," Pharm Res. 20(3):409-416 (2003).
Kreuter, Nanoparticulate carriers for drug delivery to the brain. Nanoparticles as Drug Carriers. Torchilin VP, 527-547 (2006).
Kumar et al., "Transvascular delivery of small interfering RNA to the central nervous system," Nature. 448(7149):39-43 (2007).
Kurzrock et al., "424 Poster ANG1005, an Angiopep-2/paclitaxel conjugate: the first clinical trial in patients with advanced cancer and brain metastases: Preliminary safety and tolerability data," Eur J Cancer. 6(12):133 (2008).
Kurzrock et al., "ANG1005, an angiopep-2/paclitaxel conjugate: the first clinical trial in patients with advanced cancer and brain metastases—preliminary safety and tolerability data," EORTC 2008, Poster 424, <http://angiochem.com/sites/default/files/publications/EORTC-NCI-AACR-2008-Solid-Tumour.pdf>, retrieved Sep. 16, 2016 (4 pages).
Kurzrock et al., "ANG1005: Results of a Phase I study in patients with advanced solid tumors and metastatic brain cancer," ACCR-NCI-EORTC International Conference: Molecular Targets and Cancer Therapeutics, Nov. 15-19, Boston MA. Mol Cancer Ther: 8(12 Suppl): B168 (2009) (2 pages).
Laccabue et al., "A novel taxane active against an orthotopically growing human glioma xenograft," Cancer. 92:3085-3092 (2001).
Lachowicz et al., "Analgesic properties of a novel brain-penetrant Angiopep-2-neurotensin derivative (ANG2002) for treating chronic pain," Program No. 173.28/AA9 2012 Neuroscience Meeting Planner, New Orleans, LA: Society for Neuroscience (2012) (5 pages).
Lai et al., "The critical component to establish in vitro BBB model: pericyte," Brain Res Rev. 50(2):258-265 (2005).
Lam et al., "A new type of synthetic peptide library for identifying ligand-binding activity," Nature. 354(6348):82-4 (1991).
Larionova et al., "Carbohydrate-containing derivatives of the trypsin-kallikrein inhibitor aprotinin from bovine organs II. inhibitor coupled to the (Carboxymethyl)dextran derivatives of D-galactose," Biol Chem Hoppe-Seyler. 366:743-748 (1985).
Larsson, "Megalin, an endocytic receptor with signalling potential," Acta Universitatis Upsaliensis Uppsala (58 pages) (2006).
Li et al., "Expression of alpha2-macroglobulin receptor/low density lipoprotein receptor-related protein on surfaces of tumour cells: a study using flow cytometry," Cancer Lett. 111(1-2):199-205 (1997).

(56) References Cited

OTHER PUBLICATIONS

Marinò et al., "Megalin-mediated transcytosis of thyroglobulin by thyroid cells is a calmodulin-dependent process," Thyroid. 10(6):461-469 (2000).
Marinò et al., "Transcytosis of retinol-binding protein across renal proximal tubule cells after megalin (gp 330)-mediated endocytosis," J Am Soc Nephrol. 12:637-648 (2001).
Markman et al., "Phase II trial of weekly single-agent paclitaxel in platinum/paclitaxel-refractory ovarian cancer," J Clin Oncol. 20(9):2365-9 (2002).
Martel et al., "Transport of apolipoproteins E and J at the blood-brain barrier relevance to Alzheimer's disease," S.T.P. Pharma Sciences. 7(1):28-36 (1997).
Mathupala, "Delivery of small-interfering RNA (siRNA) to the brain," available in PMC Feb. 1, 2010, published in final edited form as: Expert Opin Ther Pat. 19(2):137-40 (2009) (6 pages).
Mazel et al., "Doxorubicin-peptide conjugates overcome multidrug resistance," Anticancer Drugs. 12(2):107-116 (2001).
Mazza et al., "Cancer and the blood-brain barrier: 'Trojan horses' for courses?" Br J Pharmacol. 155(2):149-51 (2008).
McCarty, "Cell biology of the neurovascular unit: implications for drug delivery across the blood-brain barrier," Assay Drug Dev Technol. 3(1):89-95 (2005).
Michaud et al., "Risks and benefits of taxanes in breast and ovarian cancer," Drug Saf. 23(5):401-28 (2000).
Moestrup et al., "Evidence that epithelial glycoprotein 330/Megalin mediates uptake of polybasic drugs," J Clin Invest. 96(3):1404-1413 (1995).
Moore et al., "The role of flexible tethers in multiple ligand-receptor bond formation between curved surfaces," Biophys J. 91(5):1675-1687 (2006).
Moroz et al., "Long-circulated polymer-aprotinin conjugates," Poster Presentations P-IV Plasminogen Activator Inhibitors. Abstract 116. pp. 37 (1996) (Abstract Only).
Muratovska et al., "Conjugate for efficient delivery of short interfering RNA (siRNA) into mammalian cells," FEBS Lett. 558:63-68 (2004).
Ngo et al., "Computational complexity: protein structure prediction, and the levinthal paradox," *The Protein Folding Problem and Tertiary Structure Prediction*, Merz, Jr. and Le Grand, 491-495 (1994).
Niola et al., "A plasmid-encoded VEGF siRNA reduces glioblastoma angiogenesis and its combination with interleukin-4 blocks tumor growth in a xenograft mouse model," Cancer Biol Ther. 5(2):174-179 (2006).
Ojima et al., "A common pharmacophore for cytotoxic natural products that stabilize microtubules," Proc Natl Acad Sci U.S.A. 96(8):4256-61 (1999).
Oldendorf, "Stereospecificity of blood-brain barrier permeability to amino acids," Am J Physiol. 224(4):967-9 (1973).
Orlando et al., "Identification of the second cluster of ligand-binding repeats in megalin as a site for receptor-ligand interactions," Proc Natl Acad Sci USA. 94(6):2368-2373 (1997).
Pan et al., "Efficient transfer of receptor-associated protein (RAP) across the blood-brain barrier," J Cell Sci. 117(21):5071-5078 (2004).
Pardridge et al., "Combined use of carboxyl-directed protein pegylation and vector-mediated blood-brain barrier drug delivery system optimizes brain uptake of brain-derived neurotrophic factor following intravenous administration," Pharm Res. 15(4):576-582 (1998).
Pardridge et al., "Selective transport of an anti-transferrin receptor antibody through the blood-brain barrier in vivo," J Pharmacol Exp Ther. 259(1):66-70 (1991).
Pardridge, "Blood-brain barrier biology and methodology," J Neurovirol. 5(6):556-569 (1999).
Pardridge, "CNS drug design based on principles of blood-brain barrier transport," J Neurochem. 70(5):1781-1792 (1998).
Pardridge, "Drug targeting to the brain," Pharm Res. 24(9):1733-1744 (2007).
Pardridge, "Vector-mediated drug delivery to the brain," Adv Drug Deliv Rev. 36(2-3):299-321 (1999).
Patel et al., "Getting into the brain: approaches to enhance brain drug delivery," CNS Drugs. 23(1):35-58 (2009).
Pathan et al. "CNS drug delivery systems: novel approaches," Recent Pat Drug Deliv Formul. 3(1):71-89 (2009).
Powell et al., "Peptide stability in drug development. II. Effect of single amino acid substitution and glycosylation on peptide reactivity in human serum," Pharm Res. 10(9):1268-73 (1993).
Prince et al., "Lipoprotein receptor binding, cellular uptake, and lysosomal delivery of fusions between the receptor-associated protein (RAP) and alpha-L-Iduronidase or Acid alpha-Glucosidase," J Biol Chem. 279(33):35037-35046 (2004).
Ramakrishnan, "The role of P-glycoprotein in the blood-brain barrier," Einstein Q J Biol Med. 19:160-165 (2003).
Raut et al., "Abstract 39. Development and characterisation of a fibrin specific MAb-aprotinin construct," Fibrinolysis. 10(Suppl. 4):15 (1996).
Rawat et al., "Lipid carriers: a versatile delivery vehicle for proteins and peptides," Yakugaku Zasshi. 128(2):269-280 (2008).
Rizo et al. "Constrained peptides: models of bioactive peptides and protein substructures," Annu Rev Biochem. 61:387-418 (1992).
Rousselle et al., "New Advances in the Transport of Doxorubicin through the Blood-Brain Barrier by a Peptide Vector-Mediated Strategy," Mol. Pharmacol. 57:679-686 (2000).
Rudikoff et al., "Single amino acid substitution altering antigen-binding specificity," Proc Natl Acad Sci U S A. 79(6):1979-83 (1982).
Régina et al., "Antitumour activity of ANG1005, a conjugate between paclitaxel and the new brain delivery vector Angiopep-2," Br J Pharmacol. 155(2):185-97 (2008).
Régina et al., "Differences in multidrug resistance phenotype and matrix metalloproteinases activity between endothelial cells from normal brain and glioma," J Neurochem. 84:316-324 (2003).
Sadeghi-aliabadi et al., "Solvent optimization on Taxol extraction from *Taxus baccata* L., using HPLC and LC-MS," DARU. 17(3):192-8 (2009).
Saito et al., "Drug delivery strategy utilizing conjugation via reversible disulfide linkages: role and site of cellular reducing activities," Adv Drug Deliv Rev. 55(2):199-215 (2003).
Scherrmann, "Drug delivery to brain via the blood-brain barrier," Vascul Pharmacol. 38(6):349-354 (2002).
Schiff et al., "Taxol stabilizes microtubules in mouse fibroblast cells," Proc Natl Acad Sci USA. 77(3):1561-5 (1980).
Schinkel, "P-Glycoprotein, a gatekeeper in the blood-brain barrier," Adv Drug Deliv Rev. 36(2-3):179-194 (1999).
Scott et al., "Searching for peptide ligands with an epitope library," Science. 249(4967):386-90 (1990).
Seidel et al., "Effects of trasylol on the blood-brain barrier in rats," Naunyn-Schmiedebergs Arch Pharmacol. 284(4):R73 (Abstract Only) (1974).
Seiden et al., "A phase II study of the MDR inhibitor biricodar (INCEL, VX-710) and paclitaxel in women with advanced ovarian cancer refractory to paclitaxel therapy," Gynecol Oncol. 86(3):302-10 (2002).
Shao et al., "Angiopep-2 modified PE-PEG based polymeric micelles for amphotericin B delivery targeted to the brain," J Control Release. 147(1):118-26 (2010).
Shibata et al., "Clearance of Alzheimer's amyloid-beta(1-40) peptide from brain by LDL receptor-related protein-1 at the blood-brain barrier," J Clin Invest. 106(12):1489-1499 (2000).
Smith, Chapter 15: Brain perfusion systems for studies of drug uptake and metabolism in the central nervous system. *Models for Assessing Drug Absorption and Metabolism*, Borchardt, Smith, and Wilson, 285-307 (1996).
Sun et al., "Co-delivery of pEGFP-hTRAIL and paclitaxel to brain glioma mediated by an angiopep-conjugated liposome," Biomaterials. 33(3):916-24 (2012).
Tamai et al., "Structure-internalization relationship for adsorptive-mediated endocytosis of basic peptides at the blood-brain barrier," J Pharmacol Exp Ther. 280(1):410-415 (1997).
Temsamani et al., "Vector-mediated drug delivery to the brain," Expert Opin Biol Ther. 1(5):773-782 (2001).

(56) References Cited

OTHER PUBLICATIONS

Terasaki et al., "New approaches to in vitro models of blood-brain barrier drug transport," Drug Discov Today. 8(20):944-954 (2003).
Triguero et al., "Capillary depletion method for quantification of blood-brain barrier transport of circulating peptides and plasma proteins," J Neurochem. 54(6):1882-1888 (1990).
Turner et al., "RNA targeting with peptide conjugates of oligonucleotides, siRNA and PNA," Blood Cells Mol Dis. 38:1-7 (2007).
Wei et al., "Retro-inverso isomer of Angiopep-2: a stable d-peptide ligand inspires brain-targeted drug delivery," Mol Pharm. 11(10):3261-3268 (2014) (8 pages).
Wells, "Additivity of mutational effects in proteins," Biochemistry. 29(37):8509-17 (1990).
Witt et al., "Peptide drug modifications to enhance bioavailability and blood-brain barrier permeability," Peptides. 22(12):2329-2343 (2001).
Xin et al., "Angiopep-conjugated poly(ethylene glycol)-co-poly(epsilon-caprolactone) nanoparticles as dual-targeting drug delivery system for brain glioma," Biomaterials. 32(18):4293-305 (2011).
Xin et al., "The brain targeting mechanism of Angiopep-conjugated poly(ethylene glycol)-co-poly(epsilon-caprolactone) nanoparticles," Biomaterials. 33(5):1673-81 (2012).
Xu et al., "In vitro and in vivo evaluation of actively targetable nanoparticles for paclitaxel delivery," Int J Pharm. 288:361-368 (2005).
Yan et al., "Imaging brain tumor by dendrimer-based optical/paramagnetic nanoprobe across the blood-brain barrier," Chem Commun. 47:8130-2 (2011).
Yepes et al., "Tissue-type plasminogen activator induces opening of the blood-brain barrier via the LDL receptor-related protein," J Clin Invest. 112(10):1533-1540 (2003).
Zhang et al., "Tat-modified leptin is more accessible to hypothalamus through brain-blood barrier with a significant inhibition of body-weight gain in high-fat-diet fed mice," Exp Clin Endocrinol Diabetes. 118(1):31-7 (2010).
Zhao et al., "Increasing the homogeneity, stability and activity of human serum albumin and interferon-alpha2b fusion protein by linker engineering," Protein Expr Purif. 61(1):73-7 (2008).
Ziske et al., "Acute transient encephalopathy after paclitaxel infusion: report of three cases," Ann Oncol. 13(4):629-31 (2002).
Zlokovic et al., "Glycoprotein 330/Megalin: probable role in receptor-mediated transport of apolipoprotein J alone and in a complex with Alzheimer disease amyloid Beta at the blood-brain and blood-cerebrospinal fluid barriers," Proc Natl Acad Sci U S A. 93:4229-4234 (1996).
Extended European Search Report for European Patent Application No. 16812334.7, dated Jan. 24, 2019 (6 pages).
Notice of Reasons for Rejection for Japanese Patent Application No. 2018-517668, dated Jun. 9, 2020 (7 pages).
Takahashi, "Clinical Features of Leptomeningeal Carcinomatosis in Solid Cancer," Journal of Niigata Cancer Center Hospital. 52(2):60-6 (2013).

\* cited by examiner

Baseline      Post-C4 (-53%)

METHODS FOR THE TREATMENT OF LEPTOMENINGEAL CARCINOMATOSIS

BACKGROUND

Leptomeningeal carcinomatosis (LC) is a rare complication of cancer in which the disease spreads to the membranes (meninges) surrounding the brain and spinal cord. LC occurs in approximately 5% of people with cancer and is usually terminal. If left untreated, median survival is 4-6 weeks; if treated, median survival is 2-3 months. LC may occur at any stage of cancer, either as a presenting sign or as a late complication, although it is associated frequently with relapse of cancer elsewhere in the body.

LC is generally considered incurable and is difficult to treat. Treatment goals generally include improvement or stabilization of the patients neurologic status, prolongation of survival, and palliation. Thus, there is a need for therapeutics and therapeutic regimens capable of treating LC.

SUMMARY OF THE INVENTION

The present invention is based on the discovery that ANG1005, a conjugate of Angiopep-2 and three molecules of paclitaxel, was successful in treating patients with leptomeningeal carcinomatosis (LC). This conjugate is able to treat patients having LC, even where the patient is not responsive to standard chemotherapeutic agents. Since cancer cells in LC are located in the CSF and/or in the meninges, to treat LC, a compound likely needs to be transported across the blood-CSF barrier, which, unlike the blood-brain barrier which is mainly comprised of endothelial cells with tight junctions, is mainly comprised of epithelial cells. It has recently been shown that the cells of the blood-CSF barrier express LRP receptors (see Fujiyoshi et al. Journal of Neurochemistry, 2011, 118:407-415). As Angiopep-2 is known to interact with the LRP receptor, it is likely able to cross the blood-CSF barrier by LRP-mediated transcytosis, thereby transporting paclitaxel to the cancer cells in the CSF and/or in the meninges.

Accordingly, the invention features a method for the treatment of leptomeningeal carcinomatosis including administering to a subject in need thereof (e.g., a subject identified as having leptomeningeal carcinomatosis or suspected of having leptomeningeal carcinomatosis, e.g., based on radiological, neurological and/or cytological evaluations) an effective amount of a compound or pharmaceutically acceptable salt thereof including: (a) a polypeptide including the sequence of Angiopep-1 (TFFYGGCRGKRNNFK-TEEY, SEQ ID NO: 1), Angiopep-2 (TFFYGGSRGKRNNFKTEEY SEQ ID NO: 2), or Angiopep-2-4D (TFFYGGS(D-R)G(D-K)(D-R)NNF(D-K)TEEY, SEQ ID NO: 3, wherein D-R refers to D-Arginine and D-K refers to D-lysine); and (b) an anticancer agent (e.g., paclitaxel), wherein the anticancer agent is conjugated to the polypeptide. In some embodiments, the compound includes a polypeptide having the sequence of Angiopep-2. In some embodiments, the anticancer agent is a taxane such as paclitaxel or docetaxel, vinblastine, vincristine, etoposide, doxorubicin, cyclophosphamide, melphalan, or chlorambucil. In some embodiments, the anticancer agent is conjugated to the polypeptide by a linker. In some embodiments, the linker has the structure:

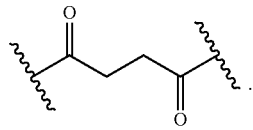 [SMILES: *C(=O)CCC(*)=O]

In some embodiments, the anticancer agent is conjugated to the polypeptide through the primary amine at the N-terminus, the primary amine of the lysine at position 10, and/or the lysine at position 15. In some embodiments, the compound has the structure:

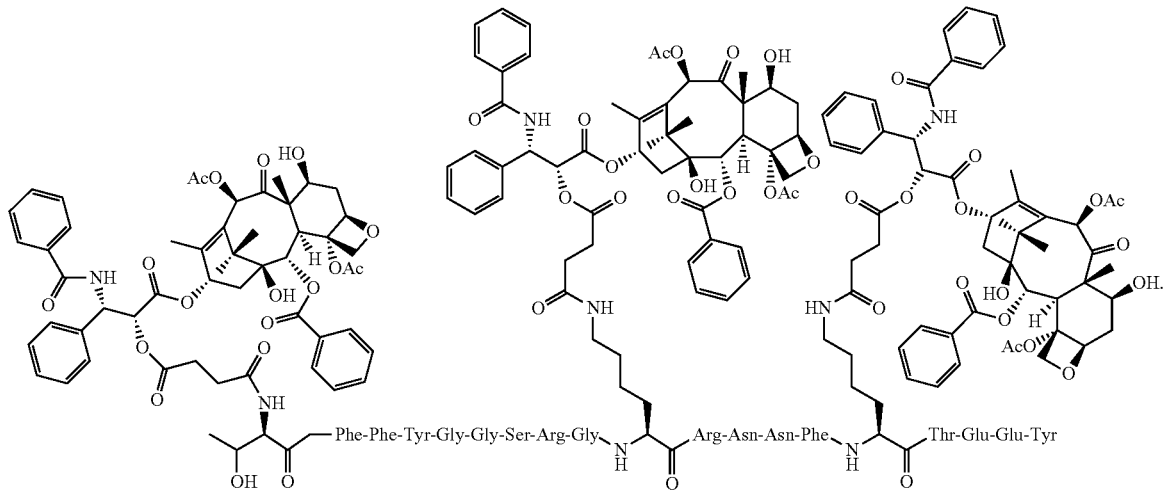

In some embodiments, the compound has the structure:

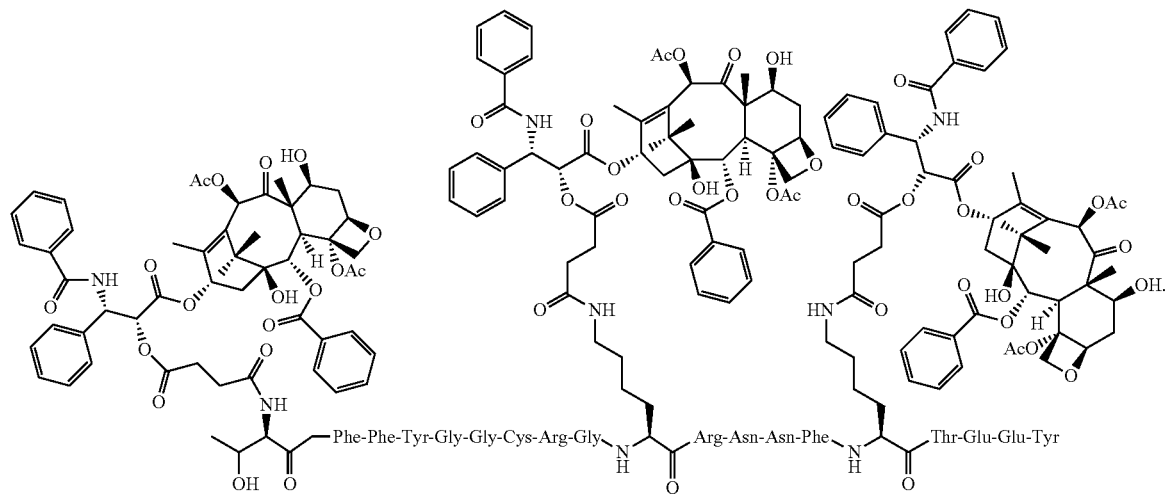

In some embodiments, the compound has the structure:

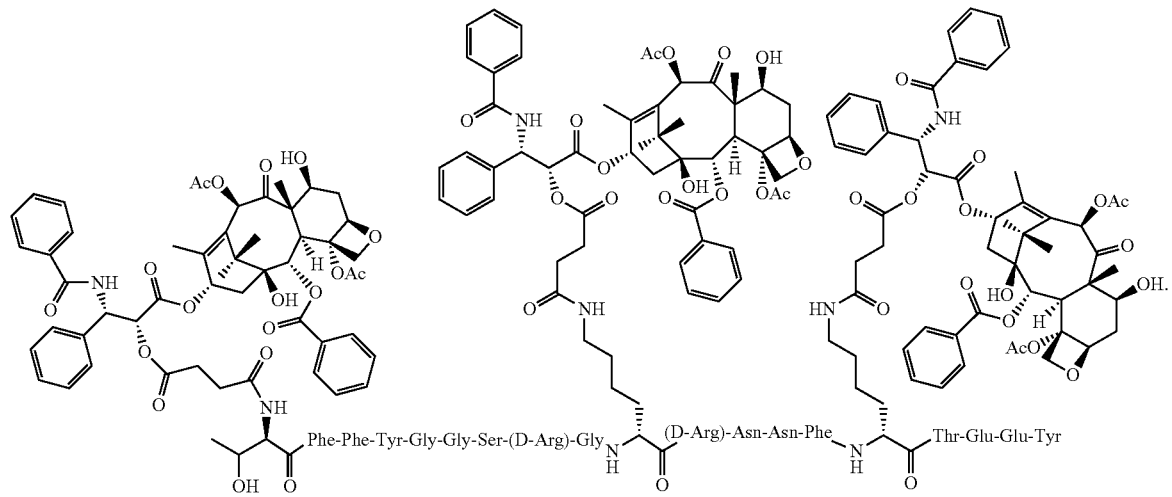

In some embodiments, the primary origin of the leptomeningeal carcinomatosis is a solid tumor (e.g., a brain tumor such a glioblastoma or medullablastoma, a breast tumor (e.g., a breast tumor identified as a HER2 positive tumor, a breast tumor identified as a HER2 negative tumor, breast tumor identified as ER positive, a breast tumor identified as ER negative, a breast tumor identified as PR positive, a breast tumor identified as PR negative, or a breast tumor identified as a triple negative breast tumor), a lung tumor such as a non-small cell lung tumor or small cell lung tumor, a gastrointestinal tumor, or malignant melanoma. In some embodiments, the primary origin of the LC is a liquid tumor (e.g., leukemia or lymphoma). In some embodiments, the primary origin of the leptomeningeal carcinomatosis is unknown (also known as cancer of unknown primary origin or occult cancer). In some embodiments, the tumor includes cells that express efflux pumps such as MDR1. In some embodiments, the primary origin of the leptomeningeal carcinomatosis is a breast tumor, e.g., a breast tumor identified as a HER2 positive tumor, a breast tumor identified as a HER2 negative tumor, breast tumor identified as ER positive, a breast tumor identified as ER negative, a breast tumor identified as PR positive, a breast tumor identified as PR negative, a breast tumor identified as HER2 positive, ER positive, and PR positive, a breast tumor identified as HER2 positive, ER positive, and PR negative, a breast tumor identified as HER2 positive, ER negative, and PR positive, a breast tumor identified as HER2 positive, ER negative, and PR negative, a breast tumor identified as ER positive, HER2 negative, and PR negative, a breast tumor identified as ER positive, HER2 negative, and PR positive, a breast tumor identified as PR positive, HER2 negative, and ER negative, or a breast tumor identified as a triple negative breast tumor. In some embodiments, the primary origin of the leptomeningeal carcinomatosis is a breast tumor, e.g., a breast tumor identified as a HER2 positive tumor, a breast tumor identified as a HER2 negative tumor, or a breast tumor identified as a triple negative breast tumor.

In some embodiments, the primary cancer has also metastasized to the liver, lungs, brain, bone, the lining of the abdomen or pelvis (peritoneum), organs of the abdomen such as the bowel, bladder, or uterus. In some embodiments, the primary cancer is in the lymph system. In some embodiments, the subject has at least one metastasis outside the brain, lung, liver, kidney, or eye.

In some embodiments, the subject previously received another anticancer therapy (e.g., an anticancer therapy including a chemotherapeutic agent such as a taxane, a platinum-based agent, an anthracycline, an anthraquinone, an alkylating agent, a HER2 targeting therapy (e.g., a HER2 antibody), vinorelbine, a nucleoside analog, ixabepilone, eribulin, cytarabine, a hormonal therapy, methotrexate, capecitabine, lapatinib, 5-FU, vincristine, etoposide, or any combination thereof). In some embodiments, the primary cancer and/or LC failed to respond to the previously received anticancer therapy and/or relapsed after the previously received anticancer therapy. In some embodiments, the primary cancer and/or LC failed to respond to the previously received anticancer therapy and/or relapsed after treatment with a taxane, e.g., paclitaxel or docetaxel. In some embodiments, the primary cancer and/or LC failed to respond to the previously received anticancer therapy and/or relapsed after treatment with methotrexate. In some embodiments, the primary cancer and/or LC failed to respond to the previously received anticancer therapy and/or relapsed after treatment with a HER2 targeting therapy. In some embodiments, the primary cancer and/or LC failed to respond to the previously received anticancer therapy and/or relapsed after treatment with a platinum-based agent. In some embodiments, the primary cancer and/or LC failed to respond to the previously received anticancer therapy and/or relapsed after treatment with an anthracycline. In some embodiments, the primary cancer and/or LC failed to respond to the previously received anticancer therapy and/or relapsed after treatment with an anthraquinone. In some embodiments, the primary cancer and/or LC failed to respond to the previously received anticancer therapy and/or relapsed after treatment with an alkylating agent. In some embodiments, the primary cancer and/or LC failed to respond to the previously received anticancer therapy and/or relapsed after treatment with vinorelbine. In some embodiments, the primary cancer and/or LC failed to respond to the previously received anticancer therapy and/or relapsed after treatment with a nucleoside analog. In some embodiments, the primary cancer and/or LC failed to respond to the previously received anticancer therapy and/or relapsed after treatment with ixabepilone. In some embodiments, the primary cancer and/or LC failed to respond to the previously received anticancer therapy and/or relapsed after treatment with eribulin. In some embodiments, the primary cancer and/or LC failed to respond to the previously received anticancer therapy and/or relapsed after treatment with cytarabine. In some embodiments, the primary cancer and/or LC failed to respond to the previously received anticancer therapy and/or relapsed after treatment with a hormonal therapy.

In some embodiments, the primary cancer and/or LC may be drug resistant (e.g., the cancer includes cells that do not respond to treatment with one or more anticancer agents) or include drug resistant cells (e.g., cells that expresses MDR1). The primary cancer and/or LC may be or may include cells that are resistant to any chemotherapeutic agent including paclitaxel, carboplatin, cisplatin, doxorubicin, topotecan, gemcitabine, docetaxel, a taxane derivative, or any agent described herein. In some embodiments, the primary cancer and/or LC is resistant to the previously received anticancer therapy.

In some embodiments, the method further includes the step of administering an additional anticancer therapy (e.g., an anticancer therapy including radiation therapy such as whole brain radiation therapy or stereotactic radiosurgery and/or a chemotherapeutic agent such as a taxane, a platinum-based agent, an anthracycline, an anthraquinone, an alkylating agent, a HER2 targeting therapy, vinorelbine, a nucleoside analog, ixabepilone, eribulin, cytarabine, a hormonal therapy, a bisphosphonate, methotrexate, capecitabine, lapatinib, 5-FU, vincristine, or etoposide). In some embodiments, the method further includes administration of methotrexate, an alkylating agent, cytarabine, or a HER2 antibody. In some embodiments, the method further includes administration of radiation therapy. In some embodiments, the additional anticancer therapy is administered before a compound of the invention. In some embodiments, the additional anticancer therapy is administered after a compound of the invention. In some embodiments, the additional anticancer therapy is administered simultaneously with a compound of the invention. In some embodiments, the method further includes the step of administering a palliative therapy, e.g., an analgesic, an anticonvulsant, an antidepressant, an anxiolytic, a psychostimulant, modafinil, palliative radiation, corticosteroids, an H1 antagonist, a hematopoietic growth factor, and/or a blood transfusion.

In some embodiments, the method includes administering a compound of the invention in a pharmaceutical composition. In some embodiments, the pharmaceutical composition includes: (a) a compound of the invention (e.g., ANG1005); (b) an optional tonicity agent; (c) a buffering agent (e.g., a buffering agent that maintains a pH of 4.5-6); (d) a bulking agent; (e) a solubilizing agent (e.g., a solubilizing agent that is not ethoxylated castor oil); and (f) 0.2 to 10% DMSO. In some embodiments, the tonicity agent is sodium chloride. In some embodiments, the buffering agent is glycine, citric acid, or lactic acid. In some embodiments, the bulking agent is mannitol or sorbitol. In some embodiments, the solubilizing agent is polyoxyethylene ester of a fatty acid (e.g., 12-Hydroxystearic acid-polyethylene glycol copolymer). In some embodiments, the composition is substantially free from ethoxylated castor oil or is free of ethoxylated castor oil. In some embodiments, the composition is dissolved in water. In some embodiments, the composition includes:

| Compound | Percentage (by non-water weight) |
| --- | --- |
| ANG1005 | 1.8-2.3% |
| Tonicity agent | 9-11% |
| Buffer (e.g., lactic acid or citric acid) | 4.5-6% |
| Bulking agent (e.g., mannitol) | 8-10% |
| 12-Hydroxystearic acid-polyethylene glycol copolymer | 69-75% |
| DMSO | 0.2-2% |

In some embodiments, the composition includes:

| Compound | Percentage (by non-water weight) |
| --- | --- |
| ANG1005 | about 2% |
| Tonicity agent | about 10% |
| Buffer (e.g., lactic acid or citric acid) | about 5% |
| Bulking agent (e.g., mannitol) | about 9% |
| 12-Hydroxystearic acid-polyethylene glycol copolymer | about 72% |
| DMSO | about 1% |

The compound or composition of the invention may be administered in a dosage of about 1, 10, 25, 50, 100, 150, 200, 250, 300, 400, 500, 600, 700, 800, 900, 1000, 1200, 1400, 1600, 1800, 2000, 2500, or 3000 mg/m$^2$, or any range between these numbers. In some embodiments, the dosage is between 100 mg/m$^2$ and 2000 mg/m$^2$ or between 300 mg/m$^2$ and 1000 mg/m$^2$. In some embodiments, the dosage is between 300 and 650 mg/m$^2$ (e.g., 550-625 mg/m$^2$). In some embodiments the dosage is between 400 and 650 mg/m$^2$. In still further embodiments the dosage is between 400 and 600 mg/m$^2$ (e.g. 400, 470, 550 or 600 mg/m$^2$). The compound of the invention may be administered by any means known in the art, e.g., intravenously, orally, intraarterially, intranasally, intraperitoneally, intramuscularly, subcutaneously, transdermally, or per os to the patient. In some embodiments, the compound is administered intravenously. In some embodiments, the compound is not administered intrathecally. In some embodiments, the compound of the invention is administered weekly (i.e., about every seven days). In some embodiments, the compound of the invention is administered bi-weekly (i.e., about every fourteen days). In some embodiments, the compound of the invention is administered tri-weekly (i.e., about every twenty one days). In some embodiments, the compound of the invention is administered at an interval of greater than twenty one days.

In some embodiments, at least one neurological symptom (e.g., headaches, gait difficulties, memory problems, incontinence, sensory abnormalities, or any neurological symptom described herein) of the subject is partially or completely alleviated, ameliorated, relieved, inhibited, delayed, or is reduced in severity after administration of a compound of the invention. In some embodiments, at least one lesion or leptomeningeal metastasis is decreased in size in the subject after administration of a compound of the invention. In some embodiments, the amount of cancer cells in the CSF is decreased in the subject after administration of a compound of the invention. In some embodiments, the flow of CSF in the subject is increased after administration of a compound of the invention.

Definitions

As used herein, the term "administration" refers to the administration of a composition (e.g., a compound, a conjugate, or a preparation that includes a compound or conjugate as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

A cancer "determined to be drug resistant," as used herein, refers to a cancer that is drug resistant, based on unresponsiveness or decreased responsiveness to a chemotherapeutic agent, or is predicted to be drug resistant based on a prognostic assay (e.g., a gene expression assay).

By a "drug resistant" cancer is meant a cancer that does not respond, exhibits a decreased response to, or is predicted to be drug resistant based on a prognostic assay (e.g., a gene expression assay) one or more chemotherapeutic agents (e.g., any agent described herein).

The term "effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "effective amount" does not in fact require successful treatment be achieved in a particular individual. Rather, an effective amount may be that amount that provides a particular desired pharmacological response in a significant number of subjects when administered to patients in need of such treatment. It is specifically understood that particular subjects may, in fact, be "refractory" to an "effective amount." To give but one example, a refractory subject may have a low bioavailability such that clinical efficacy is not obtainable. In some embodiments, reference to an effective amount may be a reference to an amount as measured in one or more specific tissues (e.g., a tissue affected by the disease, disorder or condition) or fluids (e.g., blood, saliva, serum, sweart, tears, urine, etc). Those of ordinary skill in the art will appreciate that, in some embodiments, an effective amount may be formulated and/or administered in a single dose. In some embodiments, an effective amount may be formulated and/or administered in a plurality of doses, for example, as part of a dosing regimen.

An "ER positive tumor," as used herein, refers to a tumor, e.g., a breast tumor, that has ER receptors on the surface of the cancer cells in the tumor and/or a tumor that expresses the gene for ER. An "ER negative tumor," as used herein, refers to a tumor, e.g., a breast tumor, that does not have ER receptors on the surface of the cancer cells in the tumor, a tumor that has a number of ER receptors below a predetermined level, or a tumor that does not express the gene for ER. The ER status of a tumor may be determined using methods known in the art, e.g., tests performed on biopsy samples such as immunohistochemistry or fluorescence in situ hybridization or by measurement of serum ER by ELISA.

As used herein, the term "failed to respond to a prior therapy" or "refractory to a prior therapy," refers to a cancer or LC that progressed despite treatment with the therapy.

A "HER2 positive tumor," as used herein, refers to a tumor, e.g., a breast tumor, that has HER2 receptors on the surface of the cancer cells in the tumor and/or a tumor that expresses the gene for HER2. A "HER2 negative tumor," as used herein, refers to a tumor, e.g., a breast tumor, that does not have HER2 receptors on the surface of the cancer cells in the tumor, a tumor that has a number of HER2 receptors below a predetermined level, or a tumor that does not express the gene for HER2. The HER2 status of a tumor may be determined using methods known in the art, e.g., tests performed on biopsy samples such as immunohistochemistry or fluorescence in situ hybridization or by measurement of serum HER2 by ELISA.

A "palliative therapy," as used herein refers to an therapy administered to a subject for the purpose of improving quality of life, e.g., by relieving one or more symptoms or side effects associated with a disease.

As used herein, the term "pharmaceutical composition" refers to an active compound, formulated together with one or more pharmaceutically acceptable carriers. In some embodiments, active compound is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Those of ordinary skill in the art are familiar with a variety of agents and materials useful as excipients.

The term "pharmaceutically acceptable salt," as use herein, refers to those salts of the compounds described here that are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use,* (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

A "PR positive tumor," as used herein, refers to a tumor, e.g., a breast tumor, that has PR receptors on the surface of the cancer cells in the tumor and/or a tumor that expresses the gene for PR. A "PR negative tumor," as used herein, refers to a tumor, e.g., a breast tumor, that does not have PR receptors on the surface of the cancer cells in the tumor, a tumor that has a number of PR receptors below a predetermined level, or a tumor that does not express the gene for PR. The PR status of a tumor may be determined using methods known in the art, e.g., tests performed on biopsy samples such as immunohistochemistry or fluorescence in situ hybridization or by measurement of serum PR by ELISA.

The term "primary origin," as used herein, refers to the organ in the body of the subject where the cancer began (e.g., the breast, lung, skin, gastrointestinal tract). The primary origin of a cancer may be identified using methods known in the art, e.g., medical imaging, examination of biopsy samples with immunohistochemistry techniques, and/or gene expression profiling.

The term "subject," as used herein, refers to a human or non-human animal (e.g., a mammal such as a non-human primate, horse, cow, or dog).

The term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

A "therapeutic regimen" refers to a dosing regimen whose administration across a relevant population is correlated with a desired or beneficial therapeutic outcome.

The term "treatment" (also "treat" or "treating"), in its broadest sense, refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be administered to a subject who does not exhibit signs of the relevant disease, disorder and/or condition and/or of a subject who exhibits only early signs of the disease, disorder, and/or condition. Alternatively or additionally, in some embodiments, treatment may be administered to a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

A "triple negative tumor," as used herein, refers to a tumor, e.g., a breast tumor, that does not have estrogen receptors, progesterone receptors, or human epidermal growth factor receptor 2 on the surface of the cancer cells in the tumor and/or does not substantially express the genes for estrogen receptor, progesterone receptor, or HER2. The ER, PR, and HER2 status of a tumor may be determined using methods known in the art, e.g., tests performed on biopsy samples such as immunohistochemistry or fluorescence in situ hybridization or by measurement of serum ER, PR, and/or HER2 by ELISA.

Other features and advantages of the invention will be apparent from the following Detailed Description, the drawings, and the claims.

DETAILED DESCRIPTION

Figure 1:
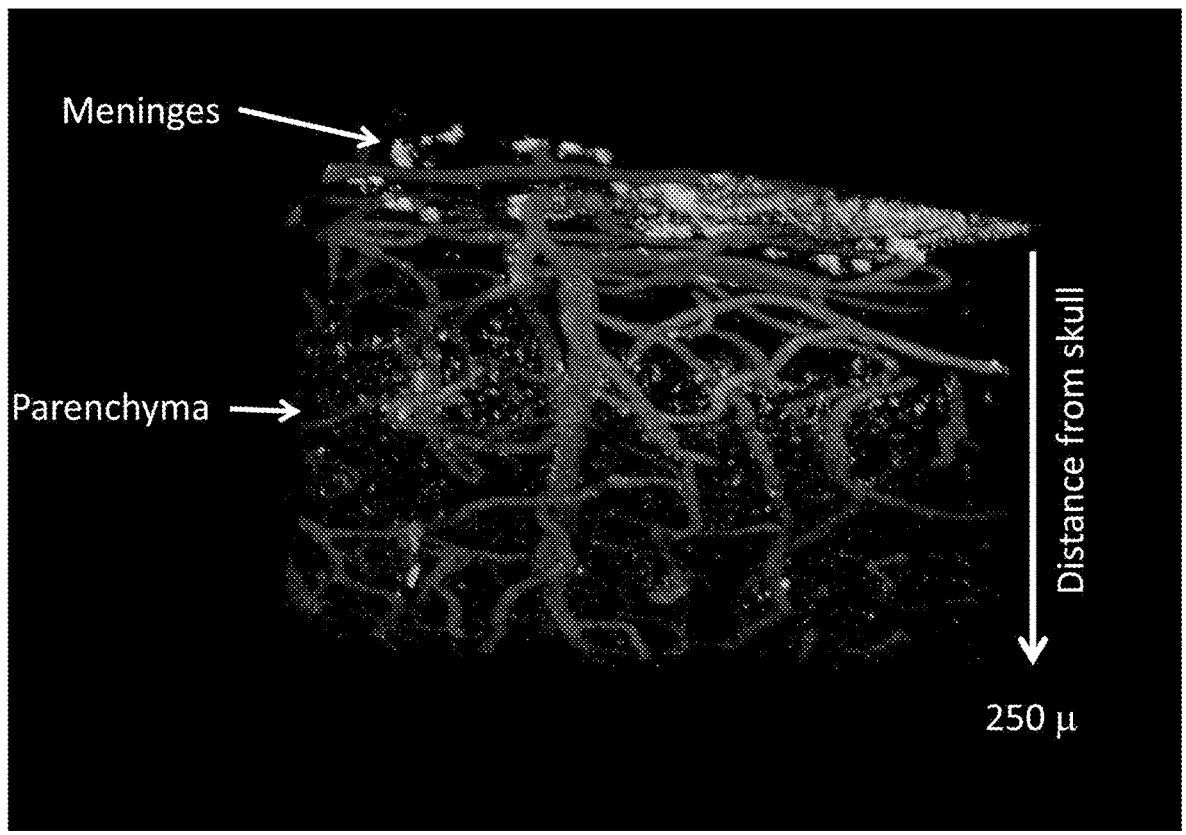
FIG. 1 is an image illustrating accumulation of an Angiopep-Cy5.5 conjugate in the meninges and parenchyma of a living mouse brain 24 hours post iv administration.

The present inventors have discovered that administration of a peptide-drug conjugate (e.g., ANG1005) is capable of treating leptomeningeal carcinomatosis (LC) in a subject. As LC is generally considered incurable, there is a need for therapeutics and therapeutic regimens capable of treating LC.

Leptomeningeal Carcinomatosis

The methods of the invention include treatment of a subject having LC. LC (also known as leptomeningeal metastasis or leptomeningeal disease) is a rare complication of cancer in which the disease spreads to the membranes (meninges) surrounding the brain and spinal cord. LC occurs in approximately 5% of people with cancer and is usually terminal. If left untreated, median survival is 4-6 weeks; if treated, median survival is 2-3 months. LC may occur at any stage of cancer, either as a presenting sign or as a late complication, though it is associated frequently with relapse of cancer elsewhere in the body.

LC occurs with invasion to and subsequent proliferation of neoplastic cells in the subarachnoid space. Malignancies of diverse origins may spread to this space, which is bound by the leptomeninges.

Spread of hematologic cancers to this space and direct CSF seeding of intraparenchymal intraaxial CNS tumors are also well recognized.

The leptomeninges consist of the arachnoid and the pia mater; the space between the two contains the CSF. When tumor cells enter the CSF (either by direct extension, as in primary brain tumors, or by hematogenous dissemination, as in leukemia), they are transported throughout the nervous system by CSF flow, causing either multifocal or diffuse infiltration of the leptomeninges in a sheetlike fashion along the surface of the brain and spinal cord. This multifocal seeding of the leptomeninges by malignant cells is LC. LC is often called lymphomatous meningitis or leukemic meningitis if the primary is not a solid tumor.

Meningeal symptoms are the first manifestations in some patients including headaches (usually associated with nausea, vomiting, light-headedness), gait difficulties from weakness or ataxia, memory problems, incontinence, and sensory abnormalities. Pain and seizures are the most common presenting complaints. CNS symptoms of LC are generally divided into three anatomic groups (1) cerebral involvement including headache, lethargy, papilledema, behavioral changes, and gait disturbance; (2) cranial-nerve involvement including impaired vision, diplopia, hearing loss, and sensory deficits, including vertigo; and cranial-nerve palsies; and (3) spinal-root involvement including nuchal rigidity and neck and back pain, or invasion of the spinal roots.

The prognosis for patients with LC is generally poor because LC usually signifies the presence of metastases elsewhere, and the course of the systemic cancer is the major determinant of the patient's survival. The exception is leukemic or lymphomatous meningitis, which is often sensitive to both methotrexate and cytarabin and often can be eradicated completely from the CNS. Among patients with LC from solid tumors, the best response to chemotherapy and radiation occurs in those with LC from breast cancer, with 60% improving or stabilizing and a median survival of 7 months; 15% survive for a year, a survival rate rare in patients with LC with a primary tumor other than breast. Only 40% of LCs from small-cell lung carcinoma improve or stabilize, and patients with this disease have a median survival of only 4 months. Melanoma-derived LC has the worst prognosis with a 3.6-month median survival, and only 20% of these patients stabilize or improve with treatment. Nonresponders to chemotherapy seldom survive longer than a month. The prognosis for LC has not improved significantly in the last 20 years despite an increase in incidence and diagnosis.

Standard Therapy for LC

Leptomeningeal carcinomatosis is generally considered incurable and is difficult to treat. Treatment goals generally include improvement or stabilization of the patients neurologic status, prolongation of survival, and palliation. Most patients require a combination of surgery, radiation, and chemotherapy. Standard therapies include radiation therapy to symptomatic sites and regions where imaging has demonstrated bulk disease and intrathecal chemotherapy (e.g., methotrexate, cytarabin, thiotepa). Radiation palliates local symptoms, relieves CSF flow obstruction, and treats areas such as nerve-root sleeves, Virchow-Robin spaces, and the interior of bulky lesions that chemotherapy does not reach. Intrathecal chemotherapy treats subclinical leptomeningeal deposits and tumor cells floating in the CSF, preventing further seeding. Supportive care for patients includes analgesia with opioids, anticonvulsants for seizures, antidepressants, and anxiolytics. Attention problems and somnolence from whole-brain radiation may be treated with psychostimulants or modafinil.

Treatment of Drug Resistant or Refractory Cancer

The patient being treated in a method of the present invention may have a cancer and/or LC that is drug resistant or refractory. Because the conjugates of the invention have activity even in cancers that have demonstrated resistance to standard chemotherapeutic agents, the methods of the invention are particularly useful in treating such drug resistant cancers and/or LC.

Drug resistance typically arises following treatment with a particular chemotherapeutic. Multiple drug resistance (MDR) can arise when a cell overproduces the p-glycoprotein (P-gp) efflux transporter. As many chemotherapeutic drugs can be P-gp substrates, including vinblastine, doxorubicin, etoposide, colchicine, and paclitaxel, overexpression of P-gp in a cancer cell can lead to broad spectrum of resistance toward chemotherapeutic agents.

The present inventors have previously shown that paclitaxel conjugated to Angiopep-1 or Angiopep-2 are not P-gp substrates and thus should not be sensitive to P-gp overexpression in tumor cells; see, e.g., pages 46-47 and FIG. 9A of International Application Publication WO 2007/009229. Thus, the drug conjugates described herein are useful in treating patients having cancer and/or LC that is resistant to standard chemotherapeutic drugs.

Enhanced Uptake into LRP Expressing Cells

The methods of the invention may be especially useful in treating cancers having cells that express low density lipoprotein-related protein (LRP) receptor. The LRP receptor is expressed on the surface of cells, and is capable of binding to various substrates including aprotinin. The polypeptides described herein were designed based on the consensus kunitz-domain sequences that act as LRP receptor ligands (see, e.g., PCT Publication No. WO 2004/060403). Uptake of the conjugates including Angiopep-1 or Angiopep-2 is inhibited by LRP ligands, thus indicating involvement of LRP in this process. Specifically, the LRP ligands RAP (200 nM) and aprotinin (10 µM) are capable of reducing brain uptake of an Angiopep conjugate. Angiopep-2 (10 or 100 µM) is similarly able to reduce uptake of the conjugates into cells.

The blood-CSF barrier has been shown to express LRP (see Fujiyoshi et al. Journal of Neurochemistry, 2011, 118: 407-415). Accordingly, LC is well suited for treatment using therapeutics that target LRP-expressing cells. As shown in FIG. 1, an Angiopep-2 conjugate is capable of accumulating in the meninges of a living mouse brain.

Combination Therapy

The methods of the invention may include administration of second therapeutic agent or treatment with a second therapy (e.g., a therapeutic agent or therapy that is standard in the art). Exemplary therapeutic agents include abarelix, aldesleukin, alemtuzumab, alitretinoin, allopurinol, altretamine, amifostine, anakinra, anastrozole, arsenic trioxide, asparaginase, azacitidine, BCG Live, bevacuzimab, bexarotene, bleomycin, bleomycin, bortezombi, bortezomib, busulfan, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin (e.g., sodium), darbepoetin alfa, dasatinib, daunorubicin, daunomycin, decitabine, denileukin, denileukin diftitox, dexrazoxane, docetaxel, doxorubicin, dromostanolone propionate, eculizumab, epirubicin (e.g., HCl), epoetin alfa, erlotinib, estramustine, etoposide (e.g., phosphate), exemestane, fentanyl (e.g., citrate), filgrastim, floxuridine, fludarabine, fluorouracil, 5-FU, fulvestrant, gefitinib, gemcitabine (e.g., HCl), gemtuzumab ozogamicin, goserelin (e.g., acetate), histrelin (e.g., acetate), hydroxyurea, ibritumomab tiuxetan, idarubicin, ifosfamide, imatinib (e.g., mesylate), Interferon alfa-2b, irinotecan, lapatinib ditosylate, lenalidomide, letrozole, leucovorin, leuprolide (e.g., acetate), levamisole, lomustine, CCNU, meclorethamine (nitrogen mustard), megestrol, melphalan (L-PAM), mercaptopurine (6-MP), mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa-2b, pemetrexed (e.g., disodium), pentostatin, pipobroman, plicamycin (mithramycin), porfimer (e.g., sodium), procarbazine, quinacrine, rasburicase, rituximab, sargramostim, sorafenib, streptozocin, sunitinib (e.g., maleate), talc, tamoxifen, temozolomide, teniposide (VM-26), testolactone, thalidomide, thioguanine (6-TG), thiotepa, thiotepa, thiotepa, topotecan (e.g., HCl), toremifene, Tositumomab/I-131 (tositumomab), trastuzumab, trastuzumab, tretinoin (ATRA), uracil mustard, valrubicin, vinblastine, vincristine, vinorelbine, vorinostat, zoledronate, and zoledronic acid. Exemplary derivatives of paclitaxel are described in U.S. Pat. No. 6,911,549, the entire contents of which are hereby incorporated by reference. Other agents include that can be used include antiestrogen agents such as tamoxifen (e.g., citrate), raloxifene, toremifene, and SCH 57068.

Polypeptide Conjugates

The methods of the invention include administration of a peptide-anticancer agent conjugate, such as those described in U.S. Patent Applications Publication Nos. 2006/0182684, and 2006/0189515, and U.S. Provisional Application No. 61/008,880, filed Dec. 20, 2007. Such conjugates may include any polypeptide described herein, an agent capable of treating LC such as paclitaxel or a paclitaxel analog (e.g., those described herein), and a linker (e.g., those described herein). Paclitaxel conjugates are exemplified by ANG1005, which includes the AngioPep-2 peptide (SEQ ID NO:97) conjugated to three paclitaxel molecules through ester linkages at the N-terminus, and through lysines at positions 10 and 15.

The conjugates, in certain embodiments, can cross the blood-brain barrier (BBB), the blood-CSF barrier, or can be preferentially targeted to certain cell types, such as breast, ovary, liver, lung, kidney, muscle cells or may be targeted to tumor cells (of any cell type described herein). The agents conjugated to these peptides can exhibit increased uptake across the BBB, which is mainly formed by endothelial cells with tight junctions, and blood-CSF barriers, which in contrast to the BBB is mainly formed by epithelial cells, and into the targeted cells, for example, by receptor-mediated endocytosis (e.g., through an LRP receptor). The conjugated agents may, either alternatively or in addition, exhibit increased stability or reduced expulsion from the cell (e.g., due to P-glycoprotein mediated efflux). Conjugates may further have activity in cancer cells that are resistant to standard chemotherapies.

Conjugates

The polypeptides described herein or derivatives thereof are conjugated to an anticancer agent (e.g., any known in the art). Each polypeptide may be conjugated to at least 1, 2, 3, 4, 5, 6, or 7 agents. In other embodiments, each agent has at least 1, 2, 3, 4, 5, 6, 7, 10, 15, 20, or more polypeptides attached thereto. The conjugates of the invention may be able to promote accumulation (e.g., due to increased uptake or reduced removal) of the agent in a particular cell type or tissue such as ovary, liver, lung, kidney, spleen or muscle of a subject.

The agent may be releasable from the vector after transport into a particular cell type or across the BBB. The agent can be released, for example, by enzymatic cleavage or other breakage of a chemical bond between the vector and the agent. The released agent may then function in its intended capacity in the absence of the vector.

In particular embodiments, the agent is paclitaxel or a paclitaxel analog (e.g., those described herein). Other anticancer agents include abarelix, aldesleukin, alemtuzumab, alitretinoin, allopurinol, altretamine, amifostine, anakinra, anastrozole, arsenic trioxide, asparaginase, azacitidine, BCG Live, bevacuzimab, bexarotene, bleomycin, bleomycin, bortezombi, bortezomib, busulfan, busulfan, calusterone, capecitabine, carboplatin, carmustine, celecoxib, cetuximab, chlorambucil, cisplatin, cladribine, clofarabine, cyclophosphamide, cytarabine, dacarbazine, dactinomycin, actinomycin D, dalteparin (e.g., sodium), darbepoetin alfa, dasatinib, daunorubicin, daunomycin, decitabine, denileukin, Denileukin diftitox, dexrazoxane, docetaxel, doxorubicin, dromostanolone propionate, eculizumab, epirubicin (e.g., HCl), epoetin alfa, erlotinib, estramustine, etoposide (e.g., phosphate), exemestane, fentanyl (e.g., citrate), filgrastim, floxuridine, fludarabine, fluorouracil, 5-FU, fulvestrant, gefitinib, gemcitabine (e.g., HCl), gemtuzumab ozogamicin, goserelin (e.g., acetate), histrelin (e.g., acetate), hydroxyurea, ibritumomab tiuxetan, idarubicin, ifosfamide, imatinib (e.g., mesylate), Interferon alfa-2b, irinotecan, lapatinib ditosylate, lenalidomide, letrozole, leucovorin, leuprolide (e.g., acetate), levamisole, lomustine, CCNU, meclorethamine (nitrogen mustard), megestrol, melphalan (L-PAM), mercaptopurine (6-MP), mesna, methotrexate, methoxsalen, mitomycin C, mitotane, mitoxantrone, nandrolone phenpropionate, nelarabine, nofetumomab, oprelvekin, oxaliplatin, paclitaxel, palifermin, pamidronate, panitumumab, pegademase, pegaspargase, pegfilgrastim, peginterferon alfa-2b, pemetrexed (e.g., disodium), pentostatin, pipobroman, plicamycin (mithramycin), porfimer (e.g., sodium), procarbazine, quinacrine, rasburicase, rituximab, sargramostim, sorafenib, streptozocin, sunitinib (e.g., maleate), talc, tamoxifen, temozolomide, teniposide (VM-26), testolactone, thalidomide, thioguanine (6-TG), thiotepa, thiotepa, thiotepa, topotecan (e.g., hcl), toremifene, Tositumomab/I-131 (tositumomab), trastuzumab, trastuzumab, tretinoin (ATRA), uracil mustard, valrubicin, vinblastine, vincristine, vinorelbine, vorinostat, zoledronate, and zoledronic acid.

Other anticancer agents include antibodies. Conjugation of such antibodies may be accomplished using any means known in the art (e.g., using the conjugation strategies described herein). Any diagnostic or therapeutic antibody may be conjugated to one or more (e.g., 2, 3, 4, 5, 6, 7, 8, 9, 10, or more) vectors of the invention. In addition, antibody fragments (e.g., capable of binding to an antigen) may also be conjugated to the vectors of the invention. Antibody fragments include the Fab and Fc regions, heavy chain, and light chain of an antibody (e.g., of any antibody described herein). Exemplary antibodies for use in diagnosis and therapy of cancer include ABX-EGF (Panitimumab), OvaRex (Oregovemab), Theragyn (pemtumomabytrrium-90), Therex, Bivatuzumab, Panorex (Edrecolomab), ReoPro (Abciximab), Bexxar (Tositumomab), MAb, idiotypic 105AD7, Anti-EpCAM (Catumaxomab), MAb lung cancer (from Cytoclonal), Herceptin (Trastuzumab), Rituxan (Rituximab), Avastin (Bevacizumab), AMD Fab (Ranibizumab), E-26 (2$^{nd}$ gen. IgE) (Omalizumab), Zevalin (Rituxan+yttrium-90) (Ibritumomab tiuxetan), Cetuximab, BEC2 (Mitumomab), IMC-1C11, nuC242-DM1, LymphoCide (Epratuzumab), LymphoCide Y-90, CEA-Cide (Labetuzumab), CEA-Cide Y-90, CEA-Scan (Tc-99m-labeled arcitumomab), LeukoScan (Tc-99m-labeled sulesomab), LymphoScan (Tc-99m-labeled bectumomab), AFP-Scan (Tc-99m-labeled), HumaRAD-HN (+yttrium-90), HumaSPECT (Votumumab), MDX-101 (CTLA-4), MDX-210 (her-2 overexpression), MDX-210/MAK, Vitaxin, MAb 425, IS-IL-2, Campath (alemtuzumab), CD20 streptavidin, Avidicin, (albumin+NRLU13), Oncolym (+iodine-131) Cotara (+iodine-131), C215 (+staphylococcal enterotoxin, MAb lung/kidney cancer (from Pharmacia Corp.), nacolomab tafenatox (C242 staphylococcal enterotoxin), Nuvion (Visilizumab), SMART M195, SMART 1D10, CEAVac, TriGem, TriAb, NovoMAb-G2 radiolabeled, Monopharm C, GlioMAb-H (+gelonin toxin), Rituxan (Rituximab), and ING-1. Additional therapeutic antibodies include 5G1.1 (Ecluizumab), 5G1.1-SC (Pexelizumab), ABX-CBL (Gavilimomab), ABX-IL8, Antegren (Natalizumab), Anti-CD11a (Efalizumab), Anti-CD18 (from Genetech), Anti-LFA1, Antova, BTI-322, CDP571, CDP850, Corsevin M, D2E7 (Adalimumab), Humira (Adalimumab), Hu23F2G (Rovelizumab), ICI4, IDEC-114, IDEC-131, IDEC-151, IDEC-152, Infliximab (Remicade), LDP-01, LDP-02, MAK-195F (Afelimomab), MDX-33, MDX-CD4, MEDI-507 (Siplizumab), OKT4A, OKT3 (Muromonab-CD3), and ReoPro (Abciximab).

Conjugation Linkers

The conjugate used in the invention may include using any cross-linking (conjugation) reagent or protocol known in the art, many of which are commercially available. Such protocols and reagents include, cross-linkers reactive with amino, carboxyl, sulfhydryl, carbonyl, carbohydrate and/or phenol groups. The amounts, times, and conditions of such protocols can be varied to optimize conjugation. Cross-linking reagents contain at least two reactive groups and are generally divided into homofunctional cross-linkers (containing identical reactive groups) and heterofunctional cross-linkers (containing non-identical reactive groups). The cross-linkers of the invention may be either homobifunctional and/or heterobifunctional. Furthermore the cross-linker may incorporate a 'spacer' between the reactive moieties, or the two reactive moieties in the cross-linker may be directly linked. Bonds may include ester bonds.

Exemplary linkers include BS$^3$ [Bis(sulfosuccinimidyl) suberate], NHS/EDC (N-hydroxysuccinimide and N-ethyl-(dimethylaminopropyl)carbodiimide, Sulfo-EMCS ([N-e-Maleimidocaproic acid]hydrazide), SATA (N-succinimidyl-S-acetylthioacetate), and hydrazide. BS$^3$ is a homobifunctional N-hydroxysuccinimide ester that targets accessible primary amines. NHS/EDC allows for the conjugation of primary amine groups with carboxyl groups. Sulfo-EMCS are heterobifunctional reactive groups (maleimide and NHS-ester) that are reactive toward sulfhydryl and amino groups. Amine coupling using sulfo-NHS/EDC activation may be used to cross-link therapeutic antibodies to polypeptides. The resulting conjugate may be stable and retain the biological activity of the antibody. Moreover, it has a high conjugation capacity that can be reliably controlled and a low non-specific interaction during coupling procedures. SATA is reactive towards amines and adds protected sulfhydryls groups. The NHS-ester reacts with primary amines to form stable amide bonds. Sulfhydryl groups may be deprotected using hydroxylamine. Hydrazide can be used to link carboxyl groups to primary amines and may therefore be useful for linking glycoproteins.

Small molecules such as therapeutic agents can be conjugated to polypeptides (e.g., those described herein). The exemplary small molecule, paclitaxel, has two strategic positions (position C2' and C7) useful for conjugation. Conjugation of a vector or vector of the invention to paclitaxel can be performed as follows. Briefly, paclitaxel is reacted with anhydride succinic pyridine for three hours at room temperature to attach a succinyl group in position 2'. The 2'-succinyl paclitaxel has a cleavable ester bond in position 2' can simply release succinic acid. This cleavable ester bond can be further used for various modifications with linkers, if desired. The resulting 2'-O-succinyl-paclitaxel is then reacted with EDC/NHS in DMSO for nine hours at room temperature, followed by the addition of the vector or vector in Ringer/DMSO for an additional reaction time of four hours at room temperature. Each intermediate, such as paclitaxel, 2'-O-succinyl-paclitaxel and 2'-O-NHS-succinyl-paclitaxel, is purified and validated using different approaches such as HPLC, thin liquid chromatography, NMR ($^{13}$C or $^1$H exchange), melting point, mass spectrometry. The final conjugate is analyzed by mass spectrometry and SDS-polyacrylamide gel electrophoresis. This allows determining the number of paclitaxel molecules conjugated on each vector.

Dosages

The dosage of any conjugate or composition described herein depends on several factors, including: the administration method, the severity of the disease, whether the cancer is to be treated or prevented, and the age, weight, and health of the subject to be treated.

With respect to the treatment methods of the invention, it is not intended that the administration of a vector, conjugate, or composition to a subject be limited to a particular mode of administration, dosage, or frequency of dosing; the invention contemplates all modes of administration. The conjugate, or composition may be administered to the subject in a single dose or in multiple doses. For example, a compound described herein or identified using screening methods of the invention may conjugate be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the composition. For example, the dosage of a composition can be increased if the lower dose does not provide sufficient activity in the treatment of a disease or condition described herein (e.g., cancer and/or LC). Conversely, the dosage of the composition can be decreased if the disease (e.g., cancer and/or LC) is reduced or eliminated.

While the attending physician ultimately will decide the appropriate amount and dosage regimen, a therapeutically effective amount of a vector, conjugate, or composition described herein, may be, for example, in the range of 0.0035 µg to 20 µg/kg body weight/day or 0.010 µg to 140 µg/kg body weight/week. Desirably a therapeutically effective amount is in the range of 0.025 µg to 10 µg/kg, for example, at least 0.025, 0.035, 0.05, 0.075, 0.1, 0.25, 0.5, 1.0, 1.5, 2.0, 2.5, 3.0, 3.5, 4.0, 5.0, 6.0, 7.0, 8.0, or 9.0 µg/kg body weight administered daily, every other day, or twice a week. In addition, a therapeutically effective amount may be in the range of 0.05 µg to 20 µg/kg, for example, at least 0.05, 0.7, 0.15, 0.2, 1.0, 2.0, 3.0, 4.0, 5.0, 6.0, 7.0, 8.0, 10.0, 12.0, 14.0, 16.0, or 18.0 µg/kg body weight administered weekly, every other week, every three weeks or once a month. Furthermore, a therapeutically effective amount of a compound may be, for example, in the range of 0.1 mg/m$^2$ to 2,000 mg/m$^2$ administered every other day, once weekly, every other week or every three weeks. For example ANG1005, may be administered at 50, 100, 200, 300, 400, 420, 500, 600, 650, 700, 800, or 1,000 mg/m$^2$ every one, two, three, four weeks, or every month or every other month. In one particular example, ANG1005 is administered at between 300 mg/m$^2$ and 650 mg/m$^2$ every three weeks. In another embodiment, the therapeutically effective amount is in the range of 1000 µg/m$^2$ to 20,000 µg/m$^2$, for example, at least 1000, 1500, 4000, or 14,000 µg/m$^2$ of the compound administered daily, every other day, twice weekly, weekly, or every other week.

Formulation of Pharmaceutical Compositions

The administration of a conjugate described herein or a composition containing the conjugate may be by any suitable means that results in a concentration of the compound that treats LC. The conjugate may be in any appropriate amount of any suitable carrier substance, and is generally present in an amount of 1-95% by weight of the total weight of the composition. The composition may be provided in a dosage form that is suitable for the oral, parenteral (e.g., intravenously or intramuscularly), rectal, cutaneous, nasal, vaginal, inhalant, skin (patch), topical, ocular, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology,* eds. J. Swarbrick and J. C. Boylan, 1988-1999, Marcel Dekker, New York).

Pharmaceutical compositions may be formulated to release the conjugate(s) immediately upon administration or at any predetermined time or time period after administration. The latter types of compositions are generally known as controlled release formulations, which include (i) formulations that create substantially constant concentrations of the conjugate(s) within the body over an extended period of time; (ii) formulations that after a predetermined lag time create substantially constant concentrations of the conjugate(s) within the body over an extended period of time; (iii) formulations that sustain the conjugate(s) action during a predetermined time period by maintaining a relatively constant, effective level of the conjugate(s) in the body with concomitant minimization of undesirable side effects associated with fluctuations in the plasma level of the conjugate(s) (sawtooth kinetic pattern); (iv) formulations that localize action of conjugate(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the conjugate(s) by using carriers or chemical derivatives to deliver the compound to a particular target cell type. Administration of the conjugate(s) in the form of a controlled release formulation is especially preferred for conjugate(s) having a narrow absorption window in the gastro-intestinal tract or a relatively short biological half-life.

Any of a number of strategies can be pursued in order to obtain controlled release in which the rate of release outweighs the rate of metabolism of the conjugate(s) in question. In one example, controlled release is obtained by appropriate selection of various formulation parameters and ingredients, including, e.g., various types of controlled release compositions and coatings. Thus, the conjugate(s) is formulated with appropriate excipients into a pharmaceutical composition that, upon administration, releases the conjugate(s) in a controlled manner. Examples include single or multiple unit tablet or capsule compositions, oil solutions, suspensions, emulsions, microcapsules, molecular complexes, microspheres, nanoparticles, patches, and liposomes.

EXAMPLES

Example 1. Treatment of LC in Breast Cancer Subjects

Method:
Twenty-eight subjects diagnosed with LC were administered 600 mg/m$^2$ of ANG1005 intravenously on a tri-weekly schedule. The subjects received between one and nine cycles of ANG1005. The receptor status of the subjects is shown in Table

TABLE 1

Receptor Status of Subjects

| Marker | Positive Patients/Negative Patients |
|---|---|
| HER2+ 17/28 | 17/28 |
| HER/− 11/28 | 11/28 |
| ER+ 16/28 | 16/28 |
| ER− 12/28 | 12/28 |
| PgR+ 13/28 | 13/28 |
| PgR− 15/28 | 15/28 |

Results:
The results of the treatment of the subjects according to CNS Response Evaluation Criteria in Solid Tumors (RECIST) based on brain parenchymal tumor response is shown in Table 2.

TABLE 2

Subject Outcomes

| Outcome | All Patients (n = 23) | HER2+ (n = 15) | HER2− (n = 8) |
|---|---|---|---|
| Partial Response (PR) | 5 (22%) | 4 (27%) | 1 (12.5%) |
| Stable Disease (SD) | 12 (52%) | 8 (53%) | 4 (50%) |
| Progressive Disease | 6 (26%) | 3 (20%) | 3 (37.5%) |
| Patient Benefit (PR + SD) | 17 (74%) | 12 (80%) | 5 (62.5%) |

As shown in Table 2, the patient benefit response rate, which includes subjects displaying a partial response or stable disease was 74%. The patient benefit response rate was 80% for subjects with HER2 positive breast cancer.

Example 2. Treatment of Subject 2

Subject 2 is a 59 year old female diagnosed in October 2012 with HER2+/ER−/PgR+infiltrating ductal carcinoma. In January 2014, Subject 2 was diagnosed with brain metastases, and in October 2014 the brain metastases relapsed with leptocarcinomatosis. Subject 2 previously received several courses of therapy including cytoxan, taxotere, and herceptin from November 2012 to March 2013, herceptin from March 2013 to October 2013, a right mastectomy in May 2013, craniotomy and SRS in February 2014, craniotomy in July 2014, and nevatinib and capecitabine in August 2014.

Subject 2 presented at the time of treatment with ANG1005 with an active tumor extending from the deep portion of the surgical cavity to the right tentorial surface and along the lateral right temporal occipital dural surface. Subject 2 started treatment with ANG1005 in October 2014 and received 7 cycles (once every three weeks). Treatment was terminated due to clinical disease progression.

The leptomeningeal carcinomatosis of Subject 2 responded to ANG1005 as indicated by a lesion in the lateral right middle cranial fossa dural surface being no longer apparent post-treatment, and a nodule of leptomeningeal metastasis just superior to the right tentorial leaflet in the inferior surface of the right hippocampal gyrus has decreasing in size.

Example 3. Treatment of Subject 3

Subject 3 is a 44 year old female diagnosed in May 2009 with HER2+/ER−/PgR− infiltrating ductal carcinoma. In March 2012, Subject 3 was diagnosed with brain metastases, and in September 2014 suffered a recurrence of the brain metastases. Subject 3 has previously received several courses of therapy including abraxane and lapatinib from May to August 2009, vinoblastine and trastuzumab from August 2012 to April 2013, WRBT in September 2012, TDM1 from April to July 2013, capecitabine and lapatinib from April to July 2014, and capecitabine and TDM1 in September 2014.

Subject 3 presented at the time of treatment with ANG1005 with numerous (>10) brain metastases all of which had increased in size despite prior treatment. Extensive scattered osseous metastatic disease in head/neck. After presenting with a numb chin (left trigeminal cranial nerve deficits), Subject 3 was also found to have leptomeningeal disease. Subject 3 started treatment with ANG1005 in September 2014 and received 5 cycles (once every three weeks). Treatment was terminated due to adverse event (pneumonia).

Figure 2A:
FIG. 2 is an image of a CT scan of a patient's brain prior to (FIG. 2A) and following (FIG. 2B) treatment with ANG1005.
Figure 2B:
Figure 3:
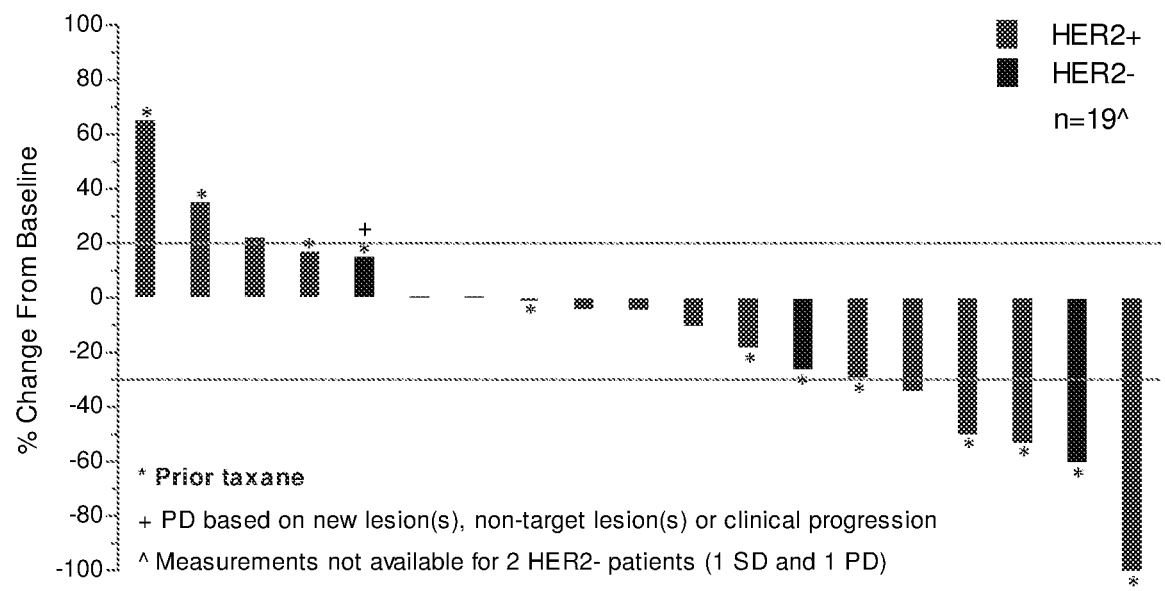
FIG. 3 is a waterfall plot of the intracranial responses to ANG1005 of patients with leptomeningeal carcinomatosis.

The leptomeningeal carcinomatosis of Subject 3 improved both radiographically and clinically. Subject 3 was able to ambulate better and had no cranial nerve or bowel/bladder symptoms after the first two cycles. As shown in FIGS. 2A and B, both the brain metastases and LC of Subject 3 responded to treatment with ANG1005.

Example 4. Treatment of Subject 4

Subject 4 is a 58 year old female diagnosed in October 2011 with HER2+/ER−/PgR− ductal carcinoma in situ. In November 2012, Subject 4 was diagnosed with brain metastases, and in March 2015 the brain metastases relapsed with leptomeningeal carcinomatosis. Subject 4 previously received several courses of therapy including carboplatin from October to November 2011, denosumab from November 2011 to November 2012, paclitaxel from December 2011 to March 2012, WBRT, transtuzumab from May 2012 to November 2012, and kadcyla from April 2013 to December 2014. Subject 4 presented at the time of treatment with ANG1005 with parenchymal metastases present in the cerebellum and widespread LC of the cerebellum and cerebral hemispheres. In addition, Subject 4 presented with mild ventricular enlargement with compression upon the fourth ventricle and outflow tracts. Subject 4 started treatment with ANG1005 in March 2015 and received 8 cycles (once every three weeks). Subject withdrew from treatment due to low performance scores.

The leptomeningeal carcinomatosis of Subject 4 responded to ANG1005 as indicated by diminished size and extent of nodular leptomeningeal enhancement related to the cerebellum with result effacement of the fourth ventricle. Furthermore, Subject 4 displayed interval decrease in volume of leptomeningeal tumor burden post-treatment.

Example 5. Treatment of Subject 8

Subject 8 is a 42 year old female diagnosed in April 2014 with HER2+/ER+/PgR− infiltrating ductal carcinoma. In December 2014, Subject 8 was diagnosed with brain metastases and in March 2015 the brain metastases recurred with leptomeningeal carcinomatosis. Subject 8 previously received several courses of therapy including docetaxel from May to October 2014, trastuzumab and pertuzumab from May to December 2014, and capecitabine and lapatinib from January to April 2015.

Subject 8 presented at the time of treatment with ANG1005 with numerous enhancing lesions throughout the supratentorial and infratentorial brain, presence of supratentorial white matter lesions, suggestive of demyelinating disease of unknown origin, CSF negative for malignant cells, and multiple stable metastases in liver. Subject 8 started treatment with ANG1005 in April 2015 and received 2 cycles (once every three weeks). Subject 8 terminated from treatment in July 2015 due to clinical progression.

The leptomeningeal carcinomatosis of Subject 8 responded to ANG1005 as indicated by improvement in extensive LC in the cerebellum.

Example 6. Kaplan-Meier Estimates of Survival for Subjects with LC

Figure 4:
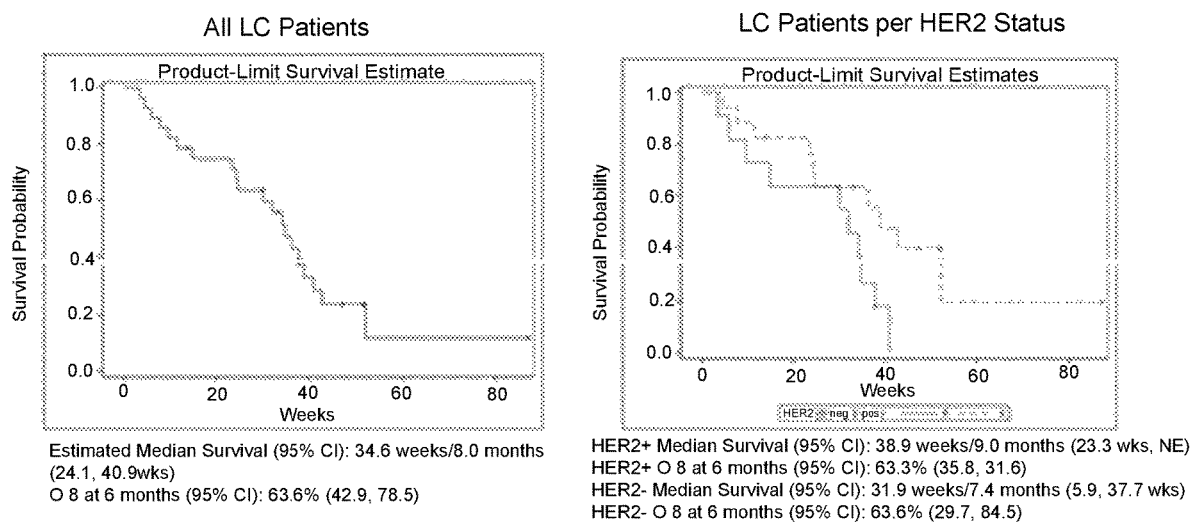
FIG. 4 is a graph of Kaplan-Meier estimates for the survival of patients with leptomeningeal cacrinomatosis treated with ANG1005.

The Kaplan-Meier method was used to estimate the overall survival of LC subjects treated with ANG1005. As shown in FIG. 4, treatment with ANG1005 was estimated to increase median overall survival compared to the historical median overall survival of 3-6 months, following aggressive treatment.

Example 7. Treatment Protocol

All patients will receive ANG1005 at a starting dose of 600 mg/m² by intravenous (IV) infusion once every 3 weeks (1 cycle). Dose reductions or delays will be allowed at any dosing cycle if toxicity is observed. Patients will be monitored during infusion and for a minimum of 1 hour after the completion of each infusion.

Intracranial and extracranial tumor evaluation by MRI/CT will be performed at baseline and after every 2 cycles (i.e., every 6±2 weeks). If a partial or complete response is seen, the subsequent MRI should be conducted at 4 weeks but 6 weeks for confirmation of response. Patients who develop extracranial disease progression in the absence of intracranial disease progression, should be removed from the study, unless the following conditions are met: (1) There is evidence of clinical benefit attributed to ANG1005 therapy, such as: (a) clinical improvement in symptoms from brain metastases, (b) radiographic improvement of brain metastases, and (2) the systemic progression is asymptomatic. However, if the Investigator decides to initiate a non-protocol systemic anti-cancer therapy as needed, then ANG1005 will be discontinued. Patients whose study treatment is discontinued before the 1 year maximum treatment period and whose disease has not progressed will continue to be followed for disease progression. Disease assessments including radiographic assessments will be done at approximately 8-week intervals, or per the institutional standard practice, starting from the date of the last dose of study treatment until intracranial and extracranial disease progression is documented. Survival follow-up will be done at approximately 8-week intervals from the date of the last dose. Patients will remain on study treatment under this protocol for a maximum period of one year unless they develop disease progression or develop unacceptable toxicity. Further treatment beyond the one year maximum period will be considered on a case-by-case basis.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

What is claimed:

1. A method for the treatment of leptomeningeal carcinomatosis comprising administering to a subject in need thereof an effective amount of a compound having the structure:

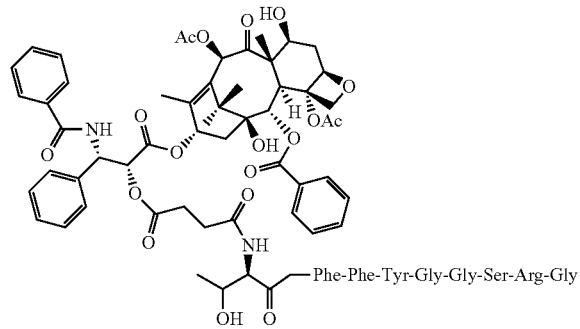

-continued

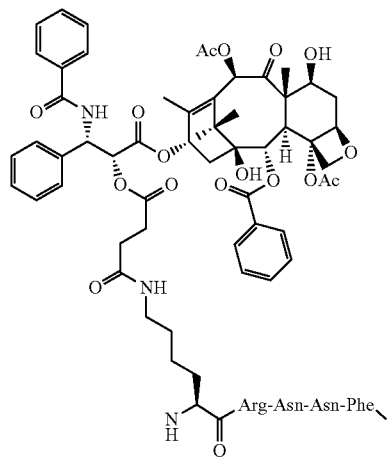

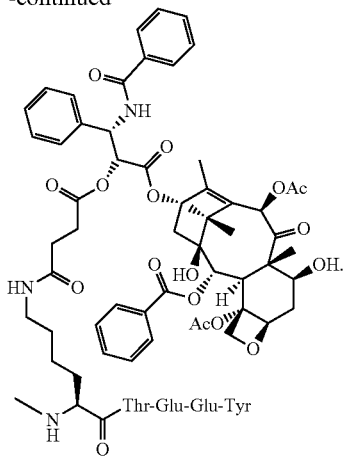

wherein said compound is administered intravenously.

2. The method of claim 1, wherein the primary origin of said leptomeningeal carcinomatosis is a solid tumor.

3. The method of claim 2, wherein said solid tumor is a breast tumor, a lung tumor, a gastrointestinal tumor, or malignant melanoma.

4. The method of claim 3, wherein said solid tumor is a breast tumor.

5. The method of claim 4, wherein said breast tumor has been identified as a HER2 positive tumor.

6. The method of claim 4, wherein said breast tumor has been identified as a triple negative tumor.

7. The method of claim 2, wherein said tumor comprises cells that express MDR1.

8. The method of claim 2, wherein said subject previously received another anticancer therapy for the leptomeningeal carcinomatosis and/or the solid tumor.

9. The method of claim 8, wherein said anticancer therapy comprises a chemotherapeutic agent.

10. The method of claim 9, wherein said chemotherapeutic agent is a taxane, a platinum-based agent, an anthracycline, an anthraquinone, an alkylating agent, a HER2 targeting therapy, vinorelbine, a nucleoside analog, ixabepilone, eribulin, cytarabine, a hormonal therapy, capecitabine, lapatinib, 5-FU, vincristine, etoposide, or methotrexate.

11. The method of claim 8, wherein the solid tumor and/or leptomeningeal carcinomatosis failed to respond to said previously received anticancer therapy and/or relapsed after treatment with said previously received anticancer therapy.

12. The method of claim 1, wherein said method further comprises administration of an additional anticancer therapy.

13. The method of claim 12, wherein said additional anticancer therapy comprises radiation therapy and/or a chemotherapeutic agent.

14. The method of claim 13, wherein said additional anticancer therapy comprises radiation therapy.

15. The method of claim 13, wherein said chemotherapeutic agent is a taxane, a platinum-based agent, an anthracycline, an anthraquinone, an alkylating agent, a HER2 targeting therapy, vinorelbine, a nucleoside analog, ixabepilone, eribulin, cytarabine, a hormonal therapy, or methotrexate.

16. The method of claim 15, wherein said chemotherapeutic agent is methotrexate, an alkylating agent, cytarabine, or a HER2 targeting therapy.

17. The method of claim 1, wherein said method further comprises administration of a palliative therapy.

18. The method of claim 17, wherein said palliative therapy is an analgesic, an anticonvulsant, an antidepressant, an anxiolytic, a psychostimulant, modafinil, palliative radiation, corticosteroids, an H1 antagonist, a hematopoietic growth factor, and/or a blood transfusion.

19. The method of claim 4, wherein said breast tumor is a HER2 negative tumor.

* * * * *

SEQUENCE LISTING

```
<160> NUMBER OF SEQ ID NOS: 3

<210> SEQ ID NO 1
<211> LENGTH: 19
<212> TYPE: PRT
<213> ORGANISM: Artificial Sequence
<220> FEATURE:
<223> OTHER INFORMATION: SYNTHETIC CONSTRUCT

<400> SEQUENCE: 1
```

```
Thr Phe Phe Tyr Gly Gly Cys Arg Gly Lys Arg Asn Asn Phe Lys Thr
1               5                   10                  15

Glu Glu Tyr

<210> SEQ ID NO 2
<211> LENGTH: 19
<212> TYPE: PRT
<213> ORGANISM: Artificial Sequence
<220> FEATURE:
<223> OTHER INFORMATION: SYNTHETIC CONSTRUCT

<400> SEQUENCE: 2

Thr Phe Phe Tyr Gly Gly Ser Arg Gly Lys Arg Asn Asn Phe Lys Thr
1               5                   10                  15

Glu Glu Tyr

<210> SEQ ID NO 3
<211> LENGTH: 19
<212> TYPE: PRT
<213> ORGANISM: Artificial Sequence
<220> FEATURE:
<223> OTHER INFORMATION: SYNTHETIC CONSTRUCT
<220> FEATURE:
<221> NAME/KEY: MISC_FEATURE
<222> LOCATION: (8)..(8)
<223> OTHER INFORMATION: Xaa is D-Arginine
<220> FEATURE:
<221> NAME/KEY: MISC_FEATURE
<222> LOCATION: (10)..(10)
<223> OTHER INFORMATION: Xaa is D-Lysine
<220> FEATURE:
<221> NAME/KEY: MISC_FEATURE
<222> LOCATION: (11)..(11)
<223> OTHER INFORMATION: Xaa is D-Arginine
<220> FEATURE:
<221> NAME/KEY: MISC_FEATURE
<222> LOCATION: (15)..(15)
<223> OTHER INFORMATION: Xaa is D-Lysine

<400> SEQUENCE: 3

Thr Phe Phe Tyr Gly Gly Ser Xaa Gly Xaa Xaa Asn Asn Phe Xaa Thr
1               5                   10                  15

Glu Glu Tyr
```